United States Patent [19]

Olliero et al.

[11] Patent Number: 4,950,661

[45] **Date of Patent: * Aug. 21, 1990**

[54] CEPHALOSPORIN DERIVATIVES, AND THEIR APPLICATION AS ANTIBIOTICS

[75] Inventors: Dominique Olliero, Montpellier; Ali Salhi, Saint-Gely-du-Fesc, both of France

[73] Assignee: SANOFI, Paris, France

[*] Notice: The portion of the term of this patent subsequent to Apr. 7, 2004 has been disclaimed.

[21] Appl. No.: 188,073

[22] Filed: Apr. 28, 1988

Related U.S. Application Data

[63] Continuation of Ser. No. 775,667, Sep. 13, 1985, abandoned.

[30] Foreign Application Priority Data

Sep. 27, 1984 [FR] France ................................ 84 14878

[51] Int. Cl.$^5$ .................. C07D 501/34; A61K 31/545

[52] U.S. Cl. .................................... 514/202; 540/222; 540/226; 540/227; 514/206; 514/207

[58] Field of Search ................ 540/227, 222; 514/206, 514/207

[56] References Cited

U.S. PATENT DOCUMENTS

| | | | |
|---|---|---|---|
| 3,647,788 | 3/1972 | Clark et al. | 540/226 |
| 3,769,277 | 10/1973 | Long et al. | 540/222 |
| 3,830,700 | 8/1974 | O'Callaghan et al. | 540/227 |
| 4,223,133 | 9/1980 | Bunnell | 540/221 X |
| 4,304,770 | 12/1981 | Takaya et al. | 540/227 X |
| 4,476,123 | 10/1984 | Labeeuw et al. | 540/227 X |
| 4,604,387 | 8/1986 | Labeeuw et al. | 540/227 X |
| 4,656,166 | 7/1987 | Salhi et al. | 540/226 X |

FOREIGN PATENT DOCUMENTS

| | | | |
|---|---|---|---|
| 1140114 | 1/1983 | Canada | 540/227 |

*Primary Examiner*—Nicholas S. Rizzo

*Attorney, Agent, or Firm*—Stevens, Davis, Miller & Mosher

[57] ABSTRACT

The present invention relates to derivatives of the cephalosporin family, of formula:

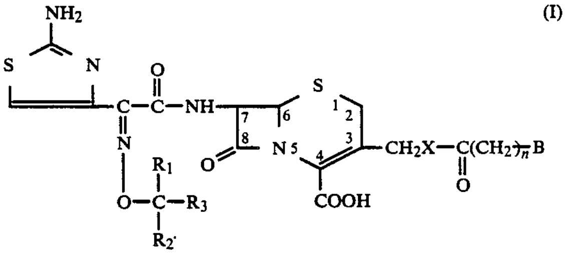

(I)

in which:

X is an oxygen atom or a sulfur atom n is zero, 1 or 2.

$R_1$, $R_2$ and $R_3$ each designate, a hydrogen atom or else $R_1$ and $R_2$ designate a hydrogen atom or a methyl group, and $R_3$ designates a carboxyl or cyclopropyl group, or else $R_1$ and $R_2$ taken together with the carbon atom to which they are linked form a cyclobutyl or cyclopentyl group and $R_3$ is a carboxyl group.

B is the residue of a primary or secondary amine;

their preparation process and application in therapeutics.

2 Claims, No Drawings

CEPHALOSPORIN DERIVATIVES, AND THEIR APPLICATION AS ANTIBIOTICS

This application is a continuation of application Ser. No. 775,667, filed Sept. 13, 1985, now abandoned.

The present invention relates to derivatives of the cephalosporin family, the process for their preparation and their therapeutic use.

The compounds according to the invention correspond to the formula:

(I)

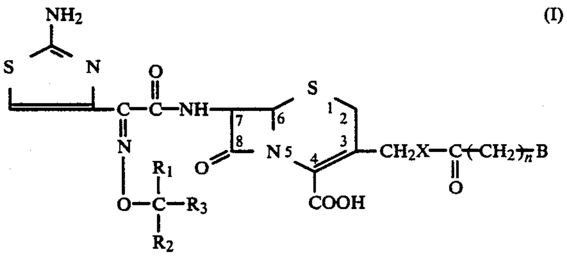

in which

X is an oxygen atom or a sulfur atom n is zero, 1 or 2.

$R_1$, $R_2$ and $R_3$ each designate, independently a hydrogen atom or else $R_1$ and $R_2$ designate a hydrogen atom or a methyl group, and $R_3$ designates a carboxyl or cyclopropyl group, or else $R_1$ and $R_2$ taken together with the carbon atom to which they are linked form a cyclobutyl or cyclopentyl group and $R_3$ is a carboxyl group.

B is the residue of a primary or secondary amine selected by the following groups:

Z—$NH_2$ where Z is an alkylene group with a straight or branched chain having from 2 to 7 carbon atoms, possibly interrupted by a sulfur atom, or else Z is a 1,3-cyclohexylene or 1,4 cyclohexylene group.

Z'—Alk—NH—R where Z' is a 1,2-phenylene or 1,3-phenylene or 1,4-phenylene group possibly substituted by 1, 2 or 3 methyl groups or else Z' is a 1,2-cyclohexylene, 1,3-cyclohexylene or 1,4-cyclohexylene group.

Alk is a straight or branched alkyl group having from 1 to 3 carbon atoms, possibly interrupted by a sulfur atom. R is a hydrogen atom or an alkyl group having from 1 to 3 carbon atoms.

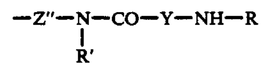

where

Z'' is a 1,3 phenylene or 1,4 phenylene group,

Y is an alkyl group $(CH_2)_m$ in which m=1,2 or 3, R' is hydrogen or methyl and R is as defined above, Z''—CO—NH—Y—$NH_2$ where Z'' and Y are as defined above Z''—NH—CO—Y—$NH_2$ where Z' is a 1,3 phenylene or 1,4 phenylene group and Y is an alkyl group $(CH_2)_m$ in which m=1,2 or 3.

Z''—Y'—NH—CO—Y—$NH_2$ where Z'' and Y are as defined above and Y' is a straight or branched alkyl group with 1 or 2 carbon atoms

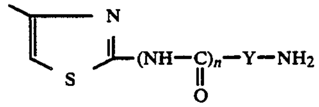

where n=0 or 1 and Y is as defined above.

a 2-piperidyl, 3-piperidyl or 4-piperidyl group possibly substituted in the nitrogen atom by a —CO—Y—$NH_2$ group where Y is as defined above.

a group

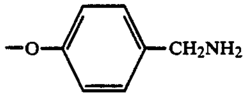

the bicyclic group

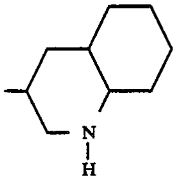

Due to the presence in the formula of an oxime group, compounds (I) exist in the two isomeric forms syn and anti. The syn isomers whose therapeutic activity is higher are the preferred compounds.

It is understood that the compound (I) indicated above can exist:

either in the form indicated in Formula (I), or in tautomeric form (I'):

(I')

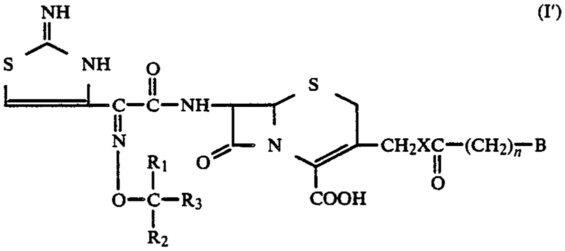

in which B, X, $R_1$, $R_2$, $R_3$ and n are as previously defined.

The salts of the compounds of Formula I (or I') are an integral part of the invention.

They are the salts with pharmaceutically acceptable acids which can form with the amine function of the molecular, as well as the alkaline, alkaline-earth salts, or the amino or aminoacid salts such as triethylamine or the ethanolamines which may form with the carboxyl group in position 4 of the compound (I), or eventually, with the carboxyl group which may be present in the oxime substituent, or else with the 2 carboxylic groups.

The same applies to the readily hydrolyzable or metabolically labile esters derivated from either or both carboxylic groups that may be present in the molecule.

The invention also relates to a process for the preparation of the compounds of Formula (I).

The compounds of Formula I may be prepared pursuant to the following reaction chart:

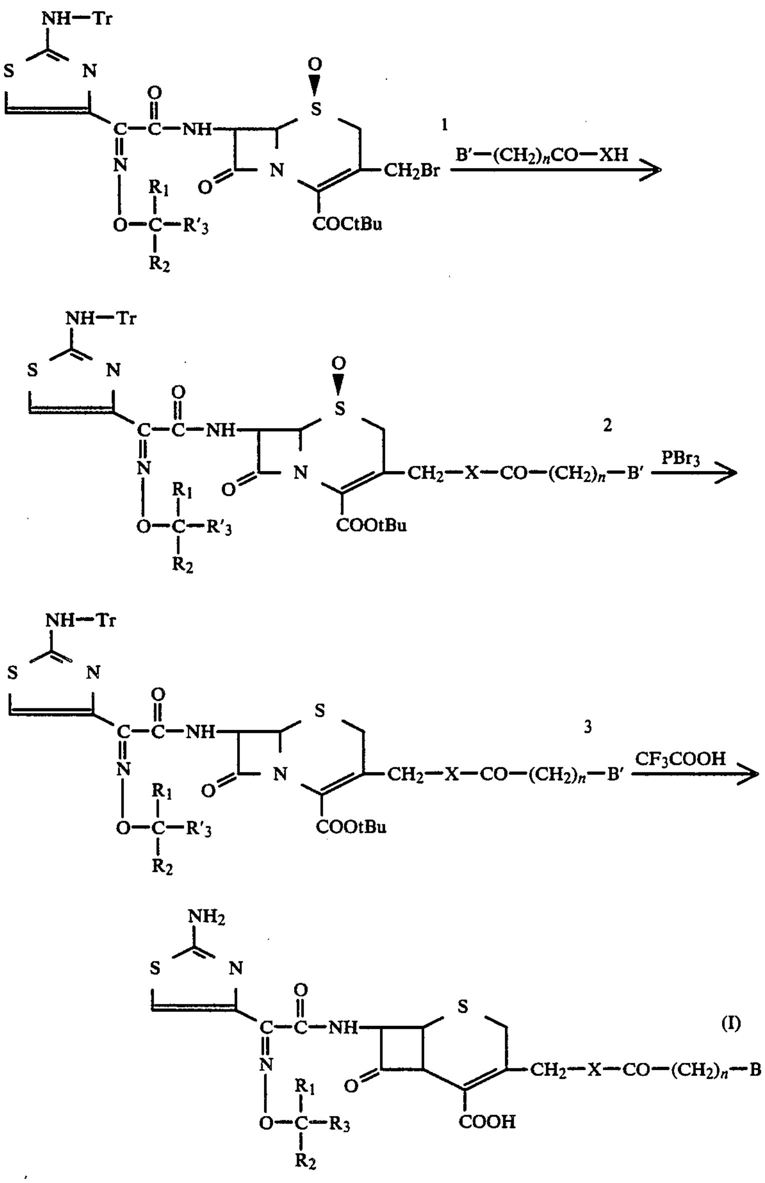

In these formulae, Tr is a protecting group of the amine function, preferably the trityl group, tBu is the tertiobutyl group, B' is the B group in which the amine function is protected and R'$_3$ is hydrogen, a cyclopropyl group or a readily labile ester group, and preferably a —COOtBu group. $R_1$, $R_2$, $R_3$, X, n and B are as previously defined.

On compound 1, the B—$(CH_2)_n$—COXH acid or thioacid is reacted; acid or thioacid, of which the amine function has been protected beforehand, according to a known method, with a group such as the tertiobutoxycarbonyl or trichloroethyoxycarbonyl group.

Mostly, the sodium salt of the acid or of the thioacid is used and the reaction is conducted in a suitable solvent such as dimethylformamide or tetrahydrofuranne.

In the case of thioacids, the thioacid itself can be used instead of its salt. Then the reaction is conducted in anhydrous acetone in the presence of potassium bicarbonate and sodium iodide.

With compound 2 obtained in this way, it is possible by the action of phosphorous tribromide at low temperature, in a solvent such as dichloromethane, to eliminate the S-oxide and to obtain compound 3.

Finally, to obtain compound (I), the protecting groups on the amines and the ester(s) are eliminated by a known method, in particular by hydrolysis in acid medium, using for example, trifluoracetic acid or a mixture of formic acid and hydrochloric acid.

Compound (I) is isolated directly in the form of a salt of the B amine group with the strong acid used for deprotection, namely in trifluoracetate or hydrochloride form. It is even possible to transform this salt into another salt of strong acid. To do so, the trifluoracetate or hydrochloride is passed over an ion-exchanging resin in the form of a weak acid (formiate or acetate for example), then the solution is treated with the strong acid from which the salt is to be obtained (for example sulfuric or phosphic acid) and the strong acid is isolated by lyophilization.

With such a salt, it is possible by the action of a base, to obtain the wanted compound of formula (I).

The starting products 1 can be prepared according to known processes and in particular by acylation of 7-amino-3-bromomethyl-3-cepheme-carboxylate or 4-tetriobutyl-1-S-oxide with the acid

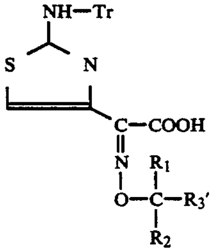

according to the process described in European Patent No. 60 745.

In the case of thioacids, (X=S), the compounds I (X=S) may be obtained by a second process. This process is summed up in the following reaction diagram:

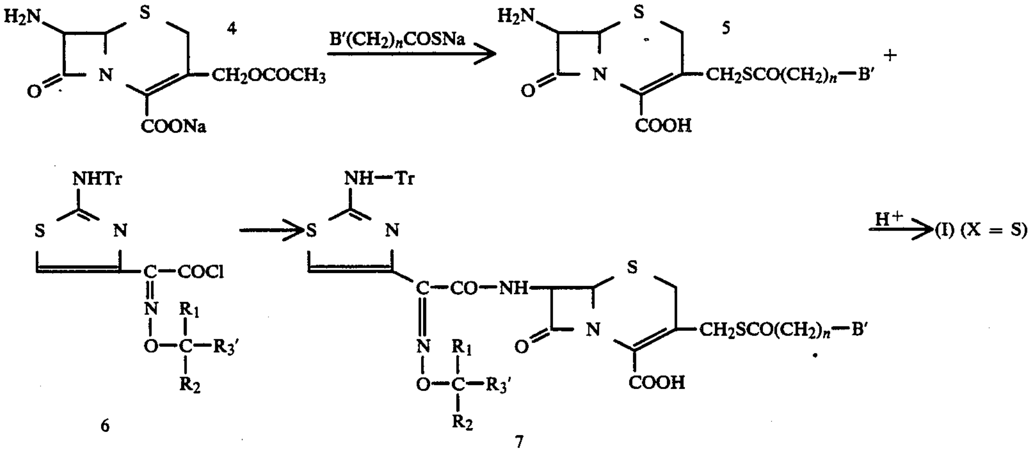

Starting with the sodium salt of 7-amino-4-cephalosporanic acid, the action of the sodium salt of the protected thioacid B'—$(CH_2)_n$—COSNa is buffered aqueous medium of pH:6.3–6.4 leads to compound 5 suitably substituted in the 3-position.

The carboxylic function being blocked in situ by a trimethylsilyl group, compound 5 is acylated by acid chloride 6. This operation is conducted in solution in the dichloromethane in the presence of triethylamine and dimethylaniline.

The protected derivatives 7 thus obtained leads to derivative (I) (X=S) by acid treatment as indicated in the first process.

The salts and esters of compounds (I) according to the invention are obtained from compounds (I) by reactions known per se.

Thus the inorganic salts are obtained by the action on compounds (I), of an inorganic base such as soda or potash or sodium bicarbonate in an equimolecular amount; the salification reaction is carried out in a solvent such as water or ethanol and the salt obtained in isolated by evaporation of the solution.

The salts of organic bases are obtained by the action on a solution of the acid I in a solvent or a mixture of suitable solvents, of an equimolecular amount of the organic base. The salt is isolated by precipitation with ether.

The esters are obtained by known esterification processes; for example the action of a halogen derivative on a salt such as the sodium salt of the acid will advantageously be used; preferably the reaction will be carried out in a solvent capable of dissolving the starting acid derivative, for example in dimethylformamide.

The syn and anti form isomers are obtained by a suitable choice of reagents.

The following examples enable the scope of the invention to be further understood without however limiting it.

Thus as is usual in this family of compounds, the products according to the invention do not have distinct melting point but only points of decomposition which do not permit them to be characterized.

The products will therefore be characterized by their nuclear magnetic resonance spectrum recorded at 250 MHz, the internal standard being hexamethyldisiloxane. The spectra are recorded in deuteriated dimethylsulfoxide: 10 mg in 0.5 ml. The chemical shifts are measured at ±0.01 ppm and the coupling constants at ±0.5 Hz.

The following abbreviations will be used:

S: singlet
D: doublet
D of D: doublet of doublet
S. e.: widened singlet
M: multiplet
Q: quadruplet
AB: AB system
J: represents the coupling constant.

In addition, elementary microanalyses were carried out in each case and are in agreement with the fomulae indicated.

The infra-red spectra also serve to characterize the products obtained. They were recorded between 4,000 $cm^{-1}$ and 600 $cm^{-1}$ from a preparation constituted by a potassium bromide tablet containing the product at a concentration of about 2%; when the spectrum is recorded in solution at 1% in a chlorinate solvent, the nature of the latter is mentioned. The elongation vibration frequency of the carbonyl groups of the molecule is noted (νCO).

EXAMPLE 1

7-[2-(2-amino 4-thiazolyl) 2-(2-carboxy 2-propyl oxyimino) acetamio] 3-(4-piperidyl carbonyloxymethyl) 3-cepheme 4-carboxylic acid bis trifluoroacetate syn isomer. SR 42800.

$R_1 = R_2 = CH_3$ $R_3 = COOH$ $X = O$ $n = O$ (I)

B = 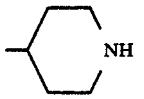

(a) 7-[2-(2-tritylamino-4-thiazolyl) 2-(2-tertiobutoxycarboxy 2-propyl oxyimino) acetamio] 3-[(1-tertiobutoxycarbonyl 4-piperidyl carbonyloxymethyl)] 3-cepheme 1 β-S-oxide 4-carboxylic of tertiobutyl, syn isomer.

To a solution of 1.38 g of 4-tertiobutyl 1-β-S-oxide 7-[2-(2-tritylamino 4-thiazolyl) 2-(2-tertiobutoxycarbonyl 2-propyl oxyimino)acetamido] 3-bromoethyl 3-cepheme carboxylate syn isomer, in 20 ml of anhydrous dimethylformamide, are added 1 g of 1-tertiobutyloxycarbonyl 4-piperidyl carboxylic acid and 1.5 g of potassium hydrogenocarbonate.

After 17 hours of stirring at ambient temperature (20°-25° C.) the reaction mixture is poured on to 200 ml of ice water. After strong stirring, the crystals are filtered and washed with water. They are taken up with 70 ml of dichloromethane. The organic phase is then washed with a saturated solution of sodium chloride, dried over magnesium sulfate and evaporated. The lacquer obtained is chromatography on a column of 50 g of silica. It is eluted with a dichloromethane-ethyl acetate mixture 90-10 (vol/vol). After evaporation of the fractions containing the compound and trituration in hexane, 1.3 of the expected compound are obtained.

IR Spectrum: νCO

1805 $cm^{-1}$: C=0 at 8-position of the β lactam
1735 $cm^{-1}$: C=0 of the tertiobutyl esters and of the ester at position 3.
1695 $cm^{-1}$: C=0 of the tertiobutoxycarbonyl protecting group of the piperidine and C=0 of the amide at 7-position.

NMR Spectrum at 250 MHz

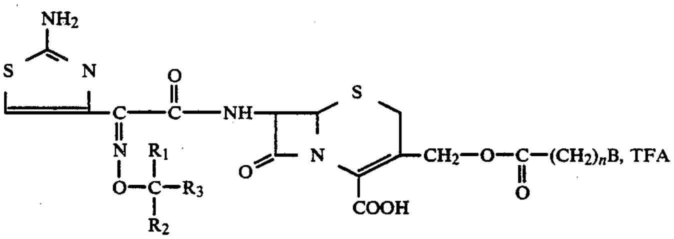

(I)

1H at 8.75 ppm (S, NH Tr) - 1H at 8.10 ppm (D, J=9 Hz, CONH) - 15H at 7.25 ppm (M, H aromatics) - 1H at 6.73 ppm (S, H thiazole) - 1H at 5.81 ppm (M, $H_7$) - 1H at 5.25 ppm (D, J=13 Hz, $CH_2$ OCO) - 1H at 4.94 ppm (D, J=4 Hz, $H_6$) - 1H at 4.55 ppm (D, J=13 Hz, $CH_2$OCO) - 1H at 3.90 ppm (D, J=17 Hz, $CH_2$SO) - 2H at 3.79 ppm (D, J=12 Hz, HCN Boc equatorials) - 1H at 3.53 ppm (D, J=17 Hz, $CH_2$SO) - 2H at 2.75 ppm (M, HCN Box axials) - 1H at 2.50 ppm (M, $HCCO_2$) - 2H at 1.75 ppm (D, J=12 Hz, $HCHCO_2$ equatorials) - 9H at 1:46 ppm (S, $CO_2$ tBu) - 2H at 1.40 ppm (M, $HCCHCO_2$ axials) - 6H at 1.39 ppm (S, $CH_3)_2$ C) - 9H at 1.36 ppm (S, $CO_2$tBu) - 9H at 1.29 ppm (S, Boc N).

(b) 7-[2-(2-tritylamino-4-thiazolyl) 2-(2-tertiobutoxycarboxy 2-propyl oxyimino) acetamio] 3-[(1-tertiobutoxycarbonyl 4-piperidyl carbonyloxymethyl)] 3-cepheme 4-carboxylic of tertiobutyl, syn isomer.

To the solution composed of 1 g of the compound obtained above and 20 ml of methylene chloride cooled down to −20° C., is added in 5 minutes, a solution of 0.15 ml of phosphorous tribromide in 20 ml of methylene chloride. Keeping the temperature down to −20° C., the mixture is stirred for 15 minutes and 100 ml of a 5% solution of sodium bicarbonate in water are added. The resulting mixture is stirred for three hours at 0° C. then the organic phase is decanted and dried over magnesium sulphate.

The solvent is evaporated in vacuo and the residual is chromatographied on silica with elution with a mixture of methylene chloride and methanol 100-0.5 vol/vol. After evaporation of the solvent, the crude product is used as in the next operation.

(c) SR 42800

The product obtained from the preceding operation is placed in solution in 15 ml of trifluoracetic acid. After 45 minutes at 25° C., the acid is evaporated in vacuo without heating and the residual is taken up in ether. The crystals are drained and washed with ether.

The expected product is obtained, after drying.

NMR Spectrum 1H at 9.45 ppm (D,J=9 Hz, —CO—NH) - 1H at 8.65 ppm and 1at 8.40 ppm (S.e., $NH_2^+$ piperidinium) - 2H at 7.30 ppm (S.E. $NH_2$ thiazole) - 1H at 6.70 ppm (S, H thiazole) - 1H at 5.80 ppm (D of D, $J_1$=9 Hz $J_2$=4 Hz $H_2$) - 1H at 5.10 ppm (D, J=4 Hz, $H_6$) - 2H at 4.99 and 4.70 ppm (D, J=13 Hz, $CH_2OCO$) - 2H at 3.52 ppm (AB, $J_{AB}$=17 Hz, $CH_2$-S) - 2H at 3.25 ppm (M, HαN piperidine) - 2H at 2.90 ppm (M, HαN piperidine) - 1H at 2.63 ppm (M, HC>-COO) - 2H at 1.95 ppm (M, Hβ N piperidine) - 2H at 1.70 ppm (Hβ N piperidine) - 6H at 1.40 ppm (2S $(CH_3)_2$—C—).

EXAMPLES 2 to 63

Operating as in Example 1, the compounds according to the invention are prepared in trifluoracetate form, as described in table 1, hereafter.

These compounds are identified by a reference number. For each one, the values of $R_1$, $R_2$, $R_3$, B and n and the NMR spectrum are given.

For 3, the last intermediate product before deblocking the acid and amine functions of the molecular, the characteristics of the infrared spectrum are also given. The wavelengths indicated in $cm^{-1}$ correspond, to the elongation vibration frequencies of the carbonyl at position 8 of the beta lactam, of the tertiobutylic esters and of the ester in position 3, of the amide in position 7 and of the carbamate protecting the amide, in this order. When only two wavelengths are indicated, the second corresponds to a wide band covering the elongation vibration frequencies of, altogether, the esters, the amide and the carbomate protecting the amine.

The list of the NMR spectra of the compounds cited in Table I is given after the Table.

TABLE I

| SR No. | n | $R_1$ | $R_2$ | $R_3$ | B | IR Intermediate 3 $\gamma CO\ cm^{-1}$ | NMR No. |
|---|---|---|---|---|---|---|---|
| 42 796 | 0 | $CH_3$ | $CH_3$ | COOH | $(CH_2)_2-NH_2$ | 1795-1725 1690 | 1 |
| 42 797 | 0 | $CH_3$ | $CH_3$ | COOH | $(CH_2)_3-NH_2$ | 1795-1725 1690 | 2 |
| 42 798 | 0 | $CH_3$ | $CH_3$ | COOH | $(CH_2)_4-NH_2$ | 1790-1725 1690 | 3 |
| 42 799 | 0 | $CH_3$ | $CH_3$ | COOH | 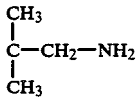 | 1795-1720 | 4 |
| 42 801 | 0 | $CH_3$ | $CH_3$ | COOH | 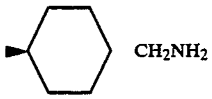 | 1790-1725 | 5 |
| 42 803 | 0 | $CH_3$ | $CH_3$ | COOH | 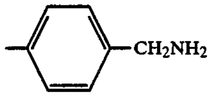 | 1790-1720 | 6 |
| 42 804 | 0 | $CH_3$ | $CH_3$ | COOH | 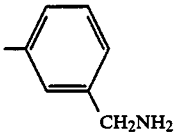 | 1790-1720 | 7 |
| 42 805 | 0 | $CH_3$ | $CH_3$ | COOH | 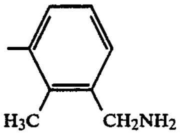 | 1790-1720 | 8 |
| 42 806 | 0 | $CH_3$ | $CH_3$ | COOH | 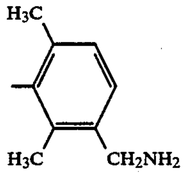 | 1795-1725 | 9 |
| 42 807 | 0 | $CH_3$ | $CH_3$ | COOH | 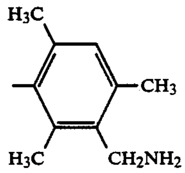 | 1795-1725 | 10 |
| 42 808 | 0 | $CH_3$ | $CH_3$ | COOH | 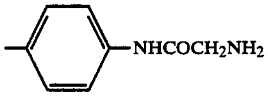 | 1790-1715 | 11 |
| 42 809 | 0 | $CH_3$ | $CH_3$ | COOH | 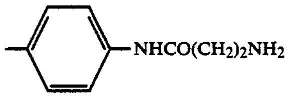 | 1795-1710 | 12 |

TABLE I-continued
| SR No. | n | $R_1$ | $R_2$ | $R_3$ | B | IR Intermediate 3 $\gamma CO\ cm^{-1}$ | NMR No. |
|---|---|---|---|---|---|---|---|
| 42 810 | 0 | $CH_3$ | $CH_3$ | COOH | 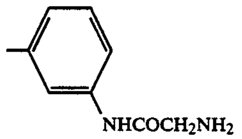 | 1790–1720 | 13 |
| 42 883 | 0 | H | H | H | 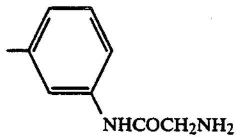 | 1790–1720<br>1690 | 14 |
| 42 885 | 0 | H | H | H | 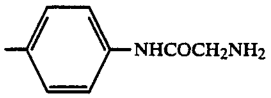 | 1790–1715 | 15 |
| 42 893 | 0 | H | H | H | 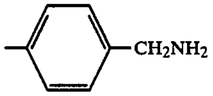 | 1790–1720 | 16 |
| 42 895 | 0 | H | H | H | 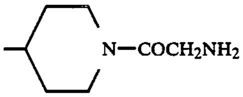 | 1790–1715<br>1655<br>($CH_2Cl_2$) | 17 |
| 42 897 | 1 | H | H | H | 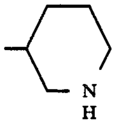 | 1790–1725<br>1680<br>($CH_2Cl_2$) | 18 |
| 42 898 | 0 | H | H | H | $CH_2SCH_2CH_2NH_2$ | 1790–1715<br>($CH_2Cl_2$) | 19 |
| 42 877 | 0 | $CH_3$ | $CH_3$ | COOH | 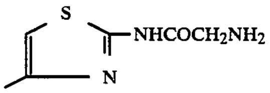 | 1790–1720 | 20 |
| 42 879 | 0 | $CH_3$ | $CH_3$ | COOH | $CH_2SCH_2CH_2NH_2$ | 1790–1715<br>($CH_2Cl_2$) | 21 |
| 42 880 | 1 | $CH_3$ | $CH_3$ | COOH | 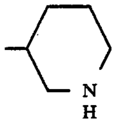 | 1790–1720<br>1680-($CH_2Cl_2$) | 22 |
| 42 881 | 0 | $CH_3$ | $CH_3$ | COOH | 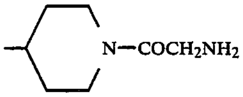 | 1790–1720<br>($CH_2Cl_2$) | 23 |
| 42 942 | 0 | $CH_3$ | $CH_3$ | COOH | 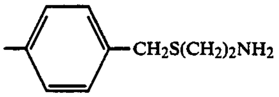 | 1790–1720 | 24 |
| 42 946 | 0 | H | H | H | 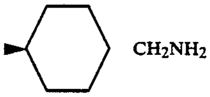 | 1790–1720 | 25 |

TABLE I-continued
| SR No. | n | R1 | R2 | R3 | B | IR Intermediate 3 γCO $cm^{-1}$ | NMR No. |
|---|---|---|---|---|---|---|---|
| 42 950 | 0 | H | H | H | 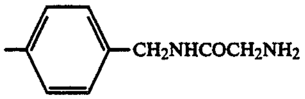 | — | 26 |
| 42 961 | 0 | $CH_3$ | $CH_3$ | COOH | 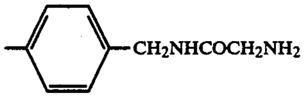 | 1790-1720<br>1680 | 27 |
| 42 963 | 0 | $CH_3$ | $CH_3$ | COOH | 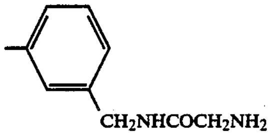 | 1790-1725 | 28 |
| 42 965 | 0 | H | H | H | 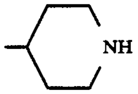 | 1790-1725<br>1685 | 29 |
| 42 971 | 0 | H | H | H | 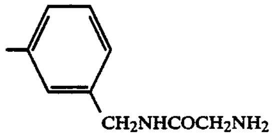 | — | 30 |
| 43 013 | 0 | $CH_3$ | $CH_3$ | COOH | 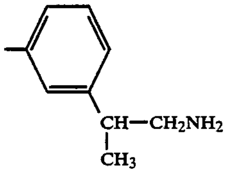 | 1790-1720 | 31 |
| 43 016 | 0 | 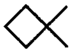 | | COOH | 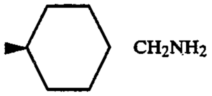 | 1795-1725 | 32 |
| 43 029 | 0 | H | H | H | 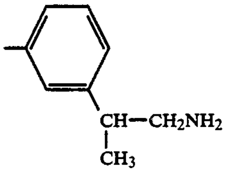 | 1785-1700 | 33 |
| 43 948 | 0 | H | H | H | 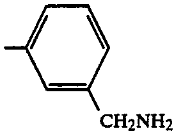 | 1790-1720 | 34 |
| 42 147 | 0 | H | H | H | 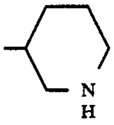 | 1790-1725<br>1625 | 35 |

TABLE I-continued
| SR No. | n | $R_1$ | $R_2$ | $R_3$ | B | IR Intermediate 3 $\gamma CO\ cm^{-1}$ | NMR No. |
|---|---|---|---|---|---|---|---|
| 43 179 | 0 | H | H | H | 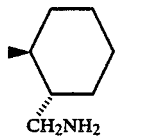 | 1790–1720 | 36 |
| 43 183 | 0 | H | H | H | 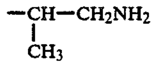 | 1790–1720 | 37 |
| 43 185 | 0 | H | H | H | 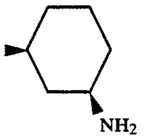 | 1790–1720 | 38 |
| 43 187 | 0 | H | H | H | 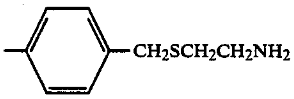 | 1790–1715 | 39 |
| 43 189 | 0 | H | H | H | 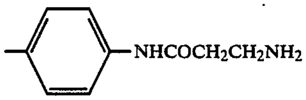 | 1790–1710 | 40 |
| 43 224 | 1 | H | H | H | 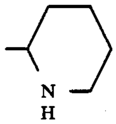 | 1790–1725<br>1680<br>($CH_2Cl_2$) | 41 |
| 43 226 | 1 | H | H | H | 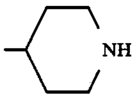 | 1790–1725<br>1680 ($CH_2Cl_2$) | 42 |
| 43 228 | 0 | H | H | H | 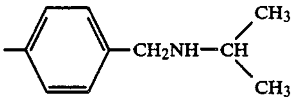 | 1790–1720<br>1685 | 43 |
| 43 230 | 0 | H | H | H | 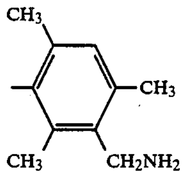 | 1785–1720 | 44 |
| 43 232 | 1 | H | H | H | 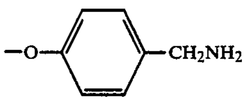 | 1785–1715<br>1685 | 45 |
| 43 323 | 0 | H | H | H | 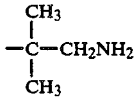 | 1790–1720 | 46 |
| 43 325 | 0 | H | H | H | 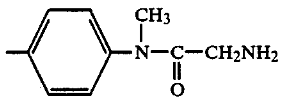 | 1790–1720<br>1675 | 47 |

TABLE I-continued
| SR No. | n | $R_1$ | $R_2$ | $R_3$ | B | IR Intermediate 3 $\gamma CO\ cm^{-1}$ | NMR No. |
|---|---|---|---|---|---|---|---|
| 43 329 | 0 | $CH_3$ | $CH_3$ | COOH | 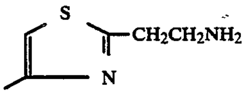 | 1790–1720 | 48 |
| 43 330 | 0 | H | H | H | 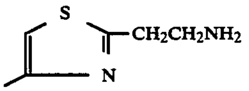 | 1785–1715 | 49 |
| 43 334 | 0 | $CH_3$ | $CH_3$ | COOH | 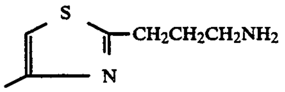 | 1790–1715 | 50 |
| 43 336 | 0 | H | H | H | 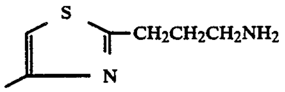 | 1785–1720 | 51 |
| 43 338 | 0 | H | H | H | 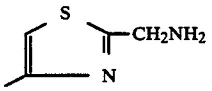 | 1785–1720 | 52 |
| 43 415 | 1 | H | H | 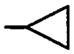 | 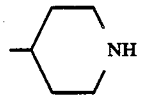 | 1780–1720<br>1680 ($CH_2Cl_2$) | 53 |
| 43 417 | 0 | H | H | H | $-(CH_2)_5NH_2$ | 1790–1720 | 54 |
| 43 419 | 0 | H | H | H | $-(CH_2)_7NH_2$ | 1790–1715<br>($CH_2Cl_2$) | 55 |
| 43 464 | 2 | H | H | H | 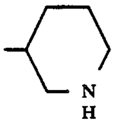 | 1785–1720<br>1665 ($CH_2Cl_2$) | 56 |
| 43 465 | 2 | $CH_3$ | $CH_3$ | COOH | 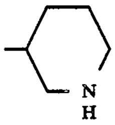 | 1785–1720<br>1675 ($CH_2Cl_2$) | 57 |
| 43 559 | 2 | H | H | H | 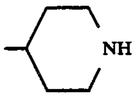 | 1790–1720<br>1680 ($CH_2Cl_2$) | 58 |
| 43 561 | 2 | $CH_3$ | $CH_3$ | COOH | 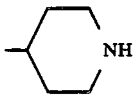 | 1790–1720<br>1675 ($CH_2Cl_2$) | 59 |
| 43 563 | 0 | $CH_3$ | $CH_3$ | COOH | 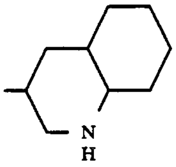 | 1785–1720<br>1685 ($CH_2Cl_2$) | 60 |
| 43 666 | 0 | H | H | H | 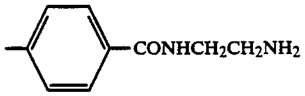 | 1785–1715<br>1685 ($CH_2Cl_2$) | 61 |

TABLE I-continued

| SR No. | n | $R_1$ | $R_2$ | $R_3$ | B | IR Intermediate 3 $\gamma$CO $cm^{-1}$ | NMR No. |
|---|---|---|---|---|---|---|---|
| 43 668 | 0 | $CH_3$ | $CH_3$ | COOH | 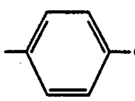 $-CONHCH_2CH_2NH_2$ | 1785-1715 1685 ($CH_2Cl_2$) | 62 |

NMR n° 1

1H at 9.41 ppm (D, J=9 Hz, CO—NH) - 3H at 7.86 ppm (S.e., $N^+H_3$) - 2H at 7.30 ppm (S.e. $NH_2$ thiazole) - 1H at 6.71 ppm (S, H thiazole) - 1H at 5.80 ppm (D of D, $J_1$=9 Hz $J_2$=4 Hz, $H_7$) - 1H at 5.09 ppm (D, J=4 Hz, $H_6$) - 1H at 5.05 ppm and 1H at 4.72 ppm (D, J=13 Hz, $CH_2OCO$) - 2H at 3.51 ppm (AB, $J_{AB}$=17 Hz, $CH_2S$) - 2H at 3.00 ppm (M, $CH_2—N^+H_3$) - 2H at 2.62 ppm (T, J=7 Hz, $CH_2—CH_2—N^+$) - 6H at 1.42 ppm (2S, $(CH_3)_2—C$).

NMR n° 2

1H at 9.45 ppm (D, J=9 Hz, CONH) - 3H at 7.75 ppm (S.e., $CH_2N^+H_3$) - 2H at 7.45 ppm (S.e. $NH_2$ thiazole) - 1H at 6.70 ppm (S, H thiazole) - 1H at 5.80 ppm (D of D, $J_1$=9 Hz $J_2$=4 Hz, $H_7$) - 1H at 5.14 ppm (D, J=4 Hz, $H_6$) - 1H at 5.05 ppm and 1H at 4.69 ppm (D, J=13 Hz, $CH_2OCO$) - 2H at 3.52 ppm (AB, $J_{AB}$=17 Hz, $CH_2S$) - 2H at 2.75 ppm (M, $CH_2N^+$) - 2H at 2.40 ppm (M, $OCOCH_2$) - 2H at 1.75 ppm (M, $CH_2—CH_2N^+$) - 6H at 1.40 ppm (2S, $(CH_3)_2—C$).

NMR n° 3

1H at 9.45 ppm (D, J=9 Hz, CONH) - 3H at 7.70 ppm (S.e., $CH_2N^+H_3$) - 2H at 7.45 ppm (S.e. $NH_2$ thiazole) - 1H at 6.70 ppm (S, H thiazole) - 1H at 5.80 ppm (D of D, $J_1$=9 Hz $J_2$=4 Hz, $H_7$) - 1H at 5.13 ppm (D, J=4 Hz, $H_6$) - 1H at 4.98 ppm and 1H at 4.65 ppm (D, J=13 Hz, $CH_2OCO$) - 2H at 3.52 ppm (AB, $J_{AB}$=17 Hz, $CH_2S$) - 2H at 2.75 ppm (M, $CH_2N^+$) - 2H at 2.35 ppm (M, $OCOCH_2$) - 4H at 1.50 ppm (M, $CH_2—CH_2—CH_2N^+$) - 6H at 1.40 ppm (2S, $(CH_3)_2—C$).

NMR n° 4

1H at 9.45 ppm (D, J=9 Hz, CONH) - 3H at 7.95 ppm (S.e., $CH_2N^+H_3$) - 2H at 7.40 ppm (S.e. $NH_2$ thiazole) - 1H at 6.70 ppm (S, H thiazole) - 1H at 5.82 ppm (D of D, $J_1$=9 Hz $J_2$=4 Hz, $H_7$) - 1H at 5.13 ppm (D, J=4 Hz, $H_6$) - 1H at 5.05 ppm and 1H at 4.70 ppm (D, J=13 Hz, $CH_2OCO$) - 2H at 3.55 ppm (AB, $J_{AB}$=17 Hz, $CH_2S$) - 2H at 2.95 ppm (M, $CH_2{}^+N$) - 6H at 1.40 ppm (2S, $(CH_3)_2C—ON$) - 6H at 1.15 ppm (S, $(CH_3)_2C—CH_2$).

NMR n° 5

1H at 9.45 ppm (D, J=9 Hz, CONH) - 3H at 7.70 ppm (S.e., $CH_2—N^+H_3$) - 2H at 7.45 ppm (S.e. $NH_2$ thiazole) - 1H at 6.70 ppm (S, H thiazole) - 1H at 5.82 ppm (D of D, $J_1$=9 Hz $J_2$=4 Hz, $H_7$) - 1H at 5.10 ppm (D, J=4 Hz, $H_6$) - 1H at 4.98 ppm and 1H at 4.65 ppm (D, J=13 Hz, $CH_2OCO$) - 2H at 3.55 ppm (AB, $J_{AB}$=17 Hz, $CH_2S$) - 2H at 2.65 ppm (M, $CH_2N^+$) - 1H at 2.25 ppm (M, $OCOCH_2$) - 4H at 1.90 ppm (M, cyclohexane) - 4H at 1.25 ppm (M, cyclohexane) - 6H at 1.40 ppm (2S, $(CH_3)_2C$) - 2H at 1.00 ppm (cyclohexane) - :

NMR n° 6

1H at 9.42 ppm (D, J=9 Hz, NHCO) - 3H at 8.30 ppm (S.e., $CH_2N^+H_3$) - 2H at 8.00 ppm (D, J=8 Hz, H aromatics ortho $CO_2$) - 2H at 7.55 ppm (D, J=8 Hz, H aromatics meta $CO_2$) - 2H at 7.30 (S.e., $NH_2$ thiazole) - 1H at 6.70 ppm (S, H thiazole) - 1H at 5.84 ppm (D of D, $J_1$=9 Hz $J_2$=4 Hz, $H_7$) - 1H at 5.16 ppm (D, J=4 Hz, $H_6$) - 1H at 4.82 ppm (D, J=13 Hz, $OCOCH_2$) - 1H at 5.25 ppm (D, J=13 Hz, O CO $CH_2$) - 2H at 4.08 ppm (M, $Ar—CH_2—NH_2$) - 2H at 3.67 ppm (AB, $J_{AB}$=17 Hz, $CH_2S$) - 6H at 1.42 ppm (2S, $(CH_3)_2—Cl$) - .

NMR n° 7

1H at 9.45 ppm (D, J=9 Hz, CONH) - 3H at 8.25 ppm (S.e., $CH_2N^+H_3$) - 1H at 8.05 ppm (S, H aromatic ortho $CO_2$ and ortho $CH_2NH_2$) - 1H at 7.95 ppm (D, J=8 Hz, H aromatic para $CH_2NH_2$) - 1at 7.70 ppm (D, J=8 Hz, H aromatic para $CO_2$) - 1H at 7.55 ppm (T, J=8 Hz, H aromatic meta $CO_2$) - 2H at 7.40 (S.e., $NH_2$ thiazole) - 1H at 6.70 ppm (S, H thiazole) - 1H at 5.85 ppm (D of D, $J_1$=9 Hz $J_2$=4 Hz, $H_7$) - 1H at 5.25 ppm (D, J=13 Hz, $CH_2OCO$) - 1H at 5.15 ppm (D, J=4 Hz, $H_6$) - 1H at 4.95 ppm (D, J=13 Hz, $CH_2OCO$) - 2H at 4.10 ppm (M, Ar $CH_2$ N) - 2H at 3.70 ppm (AB, $J_{AB}$=17 Hz, $CH_2S$) - 6H at 1.40 ppm (2S, $(CH_3)_2—C$) - .

NMR n° 8

1H at 9.45 ppm (D, J=9 Hz, CONH) - 3H at 8.25 ppm (S.e., $CH_2N^+H_3$) - 1H at 7.70 ppm (D, J=8 Hz, H aromatic ortho $CO_2$) - 1H at 7.55 ppm (D, J=8 Hz, H aromatic para $CO_2$) - 1H at 7.35 ppm (T, J=8 Hz, H aromatic meta $CO_2$) - 2H at 7.30 (se, $NH_2$ thiazole) - 1H at 6.70 ppm (S, H thiazole) - 1H at 5.85 ppm (D de D, $J_1$=9 Hz $J_2$=4 Hz, $H_7$) - 1H at 5.17 ppm (M, $H_6$ $CH_2OCO$) - 1H at 4.90 ppm (D, J=13 Hz, $CH_2OCO$) - 2H at 4.08 ppm (M, Ar $CH_2$ N) - 2H at 3.65 ppm (AB, $J_{AB}$=17 Hz, $CH_2S$) - 3H at 2.40 ppm (S, $CH_3—Ar$) - 6H at 1.40 ppm (2S, $(CH_3)_2—C$) - .

NMR n° 9

1H at 9.45 ppm (D, J=9 Hz, NHCO) - 3H at 8.15 ppm (S.e., $CH_2NH_3{}^+$) - 2H at 7.40 ppm (S.e., $NH_2$ thiazole) - 1H at 7.30 ppm (D, J=8 Hz, H aromatic para $CO_2$) - 1H at 7.15 ppm (D, J=8 Hz, H aromatic meta $CO_2$) - 1H at 6.70 ppm (S, H thiazole) - 1H at 5.85 ppm (D of D, $J_1$=9 Hz $J_2$=4 Hz, $H_7$) - 2H at 5.15 ppm (M, $H_6$ $CH_2OCO$) - 1H at 4.98 ppm (D, J=13 Hz, $CH_2OCO$) - 2H at 4.00 ppm (M, Ar $CH_2$ N) - 2H at 3.60 ppm (AB, $J_{AB}$=17 Hz, $CH_2S$) - 2H at 2.20 ppm (S, $2CH_3—Ar$) - 6H at 1.40 ppm (2S, $(CH_3)_2—C$) - .

NMR n° 10

1H at 9.43 ppm (D, J=9 Hz, CONH) - 3H at 8.00 ppm (S.e., $CH_2—N^+H_3$) - 2H at 7.40 ppm (S.e., $NH_2$ thiazole) - 1H at 7.00 ppm (S, H aromatic) - 1H at 6.70 ppm (S, H thiazole) - 1H at 5.85 ppm (D of D, $J_1$=9 Hz $J_2$=4 Hz, $H_7$) - 2H at 5.15 ppm (M, $H_6$ $CH_2OCO$) - 1H at 5.00 ppm (D, J=13 Hz, $CH_2OCO$) - 2H at 4.00 ppm (M, $CH_2N$) - 2H at 3.55 ppm (AB, $J_{AB}$=17 Hz, $CH_2S$) - 2H at 2.20 ppm (S, $CH_3$ Ar) - 3H at 2.25 ppm (S, $CH_3$ Ar) - 3H at 2.75 ppm (S, $CH_3$ Ar) - 6H at 1.40 ppm (2S $(CH_3)_2$—C) - .

NMR n° 11

1H at 10.8 ppm (S, Ar NHCO) - 1H at 9.45 ppm (D, J=9 Hz, NHCO) - 3H at 8.15 ppm (S.e., $CH_2N^+H_3$) - 1H at 7.30 ppm (D, J=8 Hz, H aromatics ortho $CO_2$) - 2H 7.67 ppm (D, J=8 Hz, H aromatics meta $CO_2$) - 2H at 7.45 ppm (S.e., $NH_2$ thiazole) - 1H at 6.70 ppm (S, H thiazole) - 1H at 5.81 ppm (D of D, $J_1$=9 Hz $J_2$=4 Hz, $H_7$) - 2H at 5.20 ppm (M, $H_6$ $CH_2OCO$) - 1H at 4.87 ppm (D, J=13 Hz, $CH_2OCO$) - 2H at 3.80 ppm (M, $COCH_2N$) - 2H at 3.68 ppm (AB, $J_{AB}$=17 Hz, $CH_2S$) - 6H at 1.43 ppm (2S, $(CH_3)_2$—C) - .

NMR n° 12

1H at 10.46 ppm (S, Ar NHCO) - 1H at 9.40 ppm (D, J=9 Hz, CONH) - 2H at 7.92 ppm (D, J=8 Hz, H aromatics ortho $CO_2$) - 5H at 7.75 ppm (M, $CH_2N^+H_3$ and H aromatics meta $CO_2$) - 2H at 7.25 ppm (S.e., $NH_2$ thiazole) - 1H at 6.71 ppm (S, H thiazole) - 1H at 5.83 ppm (D of D, $J_1$=9 Hz $J_2$=4 Hz, $H_7$) - 2H at 5.20 ppm (M, $H_6$ and $CH_2OCO$) - 1H at 4.88 ppm (D, J=13 Hz, $CH_2OCO$) - 2H at 3.65 ppm (AB, $J_{AB}$=17 Hz, $CH_2S$) - 2H at 3.05 ppm (M, $CH_2CH_2N$) - 2H at 2.72 ppm (T, J=7 Hz, $CH_2CH_2N$) - 6H at 1.40 ppm (2S, $(CH_3)_2$—C) - .

NMR n° 13

1H at 10.70 ppm (S, Ar NHCO) - 1H at 9.40 ppm (D, J=9 Hz, CONH) - 4H at 8.18 ppm (S.e., $CH_2N^+H_3$ and H aromatic ortho $CO_2$ and ortho NH) - 1H at 7.85 ppm (D, J=8 Hz, H aromatic para NH) - 1H at 7.67 ppm (D, J=8 Hz, H aromatic para $CO_2$) - 1H at 7.50 ppm (T, J=8 Hz, H aromatics meta $CO_2$) - 1H at 6.70 ppm (S, H thiazole) - 1H at 5.80 ppm (D of D, $J_1$=9 Hz $J_2$=4 Hz, $H_7$) - 1H at 5.25 ppm (D, J=13 Hz, $CH_2OCO$) - 1H at 5.15 ppm (D, J=4 Hz, $H_6$) - 1H at 4.90 ppm (D, J=13 Hz, $CH_2OCO$) - 2H at 3.75 ppm (M, CO—$CH_2$—N) - 2H at 3.68 ppm (AB, $J_{AB}$=17 Hz, $CH_2S$) - 6H at 1.43 ppm (2S, $(CH_3)_2$—C) - .

NMR n° 14

1H at 10.70 ppm (S, Ar NHCO) - 1H at 9.55 ppm (D, J=9 Hz, NH—CO) - 4H at 8.18 ppm (S.e., $CH_2N^+H_3$, H aromatic ortho $CO_2$ and ortho NH) - 1H at 7.82 ppm (D, J=8 Hz, H aromatic para NH) - 1H at 7.72 ppm (D, J=8 Hz, H aromatic para $CO_2$) - 1H at 7.50 ppm (T, J=8 Hz, H aromatics meta $CO_2$) - 2H at 7.20 ppm (S.e., $NH_2$ thiazole) - 1H at 6.69 ppm (S, H thiazole) - 1H at 5.80 ppm (D of D, $J_1$=9 Hz $J_2$=4 Hz, $H_7$) - 1H at 5.25 ppm (D, J=13 Hz, $CH_2OCO$) - 1H at 5.15 ppm (D, J=4 Hz, $H_6$) - 1H at 4.93 ppm (D, J=13 Hz, $CH_2OCO$) - 5H at 3.80 ppm (2S, $CH_3ON$ and $COCH_2N$) - 2H at 3.63 ppm (AB, $J_{AB}$=17 Hz, $CH_2S$) - .

NMR n° 15

1H at 10.80 ppm (S, Ar—NH—CO) - 1H at 9.55 ppm (D, J=9 Hz, CONH) - 3H at 8.20 ppm (S.e., $CH_2N^+H_3$) - 2H at 7.95 ppm (D, J=8 Hz, H aromatic ortho $CO_2$) - 2H at 7.70 (D, J=8 Hz, H aromatic meta $CO_2$) - 2H at 7.20 ppm (S.e., $NH_2$ thiazole) - 1H at 6.70 ppm (S, H thiazole) - 1H at 5.75 ppm (D of D, $J_1$=9 Hz $J_2$=4 Hz, $H_7$) - 1H at 5.20 ppm (D, J=13 Hz, $CH_2OCO$) - 1H at 5.10 ppm (D, J=4 Hz, $H_6$) - 1H at 4.92 ppm (D, J=13 Hz, $CH_2OCO$) - 5H at 3.85 ppm (S.e., N—$OCH_3$ and $COCH_2N$) - 2H at 3.60 ppm (AB, $J_{AB}$=17 Hz, $CH_2S$) - .

NMR n° 16

1H at 9.60 ppm (D, J=9 Hz, NHCO) - 3H at 8.30 ppm (S.e., $CH_2N^+H_3$) - 2H at 7.97 ppm (D, J=8 Hz, H aromatics ortho $CO_2$) - 2H at 7.55 ppm (D, J=8 Hz, H aromatics meta $CO_2$) - 2H at 7.20 ppm (S.e., $NH_2$ thiazole) - 1H at 6.70 ppm (S, H thiazole) - 1H at 5.75 ppm (D of D, $J_1$=9 Hz $J_2$=4 Hz, $H_7$) - 1H at 5.25 ppm (D, J=13 Hz, $CH_2OCO$) - 1H at 5.13 ppm (D, J=4 Hz, $H_6$) - 1H at 4.93 ppm (D, J=13 Hz, $CH_2OCO$) - 2H at 4.09 ppm (M, Ar $CH_2$ N) - 3H at 3.80 ppm (S, $CH_3ON$) - 2H at 3.66 ppm (AB, $J_{AB}$=17 Hz, $CH_2S$) - .

NMR n° 17

1H at 9.55 ppm (D, J=9 Hz, CONH) - 3H at 8.00 ppm (S.e., $CH_2N^+H_3$) - 1H at 6.70 ppm (S, H thiazole) - 1H at 5.76 ppm (D of D, $J_1$=9 Hz $J_2$=4 Hz, $H_7$) - 1H at 5.09 ppm (D, J=4 Hz, $H_6$) - 1H at 4.97 ppm and 1H at 4.68 ppm ((D, J=13 Hz, $CH_2OCO$) - 1H at 4.12 ppm (M, H piperidine α N equatorial) - 5H at 3.80 ppm (M, $CH_3ON$ et CO—$CH_2N$) - 3H at 3.50 ppm (M, $CH_2S$ et H piperidine α N equatorial) - 1H at 3.05 ppm (M, H piperidine α N axial) - 1H at 2.80 ppm (M, H piperidine α N axial) - 1H at 2.66 ppm (M, H piperidine γ N) - 2H at 1.85 ppm and 2H at 1.50 ppm (M, H piperidine β N) - .

NMR n° 18

1H at 9.55 ppm (D, J=9 Hz, NHCO) - 1H at 8.50 ppm and 1H at 8.40 ppm (S.e., $N^+H_2$ piperidinium) - 2H at 7.30 ppm (S.e., $NH_2$ thiazole) - 1H at 6.70 ppm (S, H thiazole) - 1H at 5.75 ppm (D of D, $J_1$=9 Hz $J_2$=4 Hz, $H_7$) - 1H at 5.08 ppm (D, J=4 Hz, $H_6$) - 1H at 4.95 ppm 1H at 4.56 ppm (D, J=13 Hz, $CH_2OCO$) - 3H at 3.80 ppm (S, $CH_3ON$) - 2H at 3.50 ppm (AB, $J_{AB}$=17 Hz, $CH_2S$) - 2H at 3.15 (M, H piperidine α N equatorial) - 2H at 2.65 ppm (M, H piperidine α N axial) - 2H at 2.36 ppm (M, $OCOCH_2$) - 1H at 2.00 ppm (M, H piperidine $CH_2$—HC<) - 4H between 1.2 and 1.7 ppm (M, H piperidine β et γ N) - .

NMR n° 19

1H at 9.58 ppm (D, J=9 Hz, NHCO) - 3H at 7.80 ppm (S.e., $CH_2NH_3^+$) - 1H at 6.71 ppm (S, H thiazole) - 1H at 5.75 ppm (D of D, $J_1$=9 Hz $J_2$=4 Hz, $H_7$) - 1H at 5.10 ppm (D, J=4 Hz, $H_6$) - 1H at 5.03 ppm 1H at 4.75 ppm (D, J=13 Hz, $CH_2OCO$) - 3H at 3.84 ppm (S, $CH_3ON$) - 1H at 3.60 ppm (D, J=17 Hz, $CH_2S$) - 3H at 3.48 ppm (M, $CH_5S$ et $OCOCH_2S$) - 2H at 3.00 ppm (M, $CH_2N^+H_3$) - 2H at 2.75 ppm (T, J=7 Hz, $CH_2$—$CH_2$—$N^+H_3$) - .

NMR n° 20

1H at 12.80 ppm (S.e., thiazole-NHCO) - 1H at 9.45 ppm (D, J=9 Hz, NHCO) - 3H at 8.40 ppm (S.e., $CH_2N^+N_3$) - 1H at 8.20 ppm (S, H thiazole ester) - 2H at 7.40 (S.e., $NH_2$ thiazole) - 1H at 6.68 ppm (S, H thiazole amine) - 1H at 5.88 ppm (D de D, $J_1$=9 Hz $J_2$=4 Hz, $H_7$) - 2H at 5.20 ppm (M, $H_6$ and $CH_2OCO$) - 1H at 4.90 ppm (D, J=13 Hz, $CH_2OCO$) - 2H at 3.84 ppm (S.e., $COCH_2N$) - 2H at 3.61 ppm (AB, $J_{AB}$=17 Hz, $CH_2S$) - 6H at 1.42 ppm (2S, $(CH_3)_2C$) - .

NMR n° 21

1H at 9.40 ppm (D, J=9 Hz, CONH) - 3H at 7.80 ppm (S.e., $CH_2N^+H_3$) - 2H at 7.40 ppm (S.e., $NH_2$ thiazole) - 1H at 6.68 ppm (S, H thiazole) - 1H at 5.85 ppm (D of D, $J_1$=9 Hz $J_2$=4 Hz, $H_7$) - 1H at 5.13 ppm (D, J=4 Hz, $H_6$) - 1H at 5.04 ppm and 1H at 4.75 ppm (D, J=13 Hz, $CH_2OCO$) - 1H at 3.60 ppm (D, J=17 Hz, $CH_2S$) - 3H at 3.50 ppm (M, $CH_2S$ et $OCOCH_2S$—) - 2H at 2.98 ppm (M, $CH_2N$) - 2H at 2.75 ppm (M, $CH_2CH_2N$) - 6H at 1.42 ppm (2S, $(CH_3)_2C$) - .

NMR n° 22

1H at 9.40 ppm (D, J=9 Hz, NHCO) - 1H at 8.60 ppm and 1H at 8.40 ppm (S.e., $N^+H_2$ piperidinium) - 1H at 6.70 ppm (S, H thiazole) - 1H at 5.83 ppm (D of D, $J_1$=9 Hz $J_2$=4 Hz, $H_7$) - 1H at 5.12 ppm (D, J=4 Hz, $H_6$) - 1H at 4.95 ppm and 1H at 4.67 ppm (D, J=13 Hz, $CH_2OCO$) - 2H at 3.50 ppm (AB, $J_{AB}$=17 Hz, $CH_2S$) - 2H at 3.20 (M, H piperidine α N equatorial) - 2H at 2.60 ppm (M, H piperidine α N axial) - 2H at 2.30 ppm (M, $OCOCH_2$) - 1H at 2.05 ppm (M, H piperidine —HC<) - 4H between 1.90 and 1.20 ppm (M, H piperidine β and γ N) - 6H at 1.44 ppm (2S, $(CH_3)_2$) - .

NMR n° 23

1H at 9.45 ppm (D, J=9 Hz, NHCO) - 3H at 8.00 ppm (S.e., $CH_2N^+H_3$) - 1H at 6.73 ppm (S, H thiazole) - 1H at 5.84 ppm (D of D, $J_1$=9 Hz $J_2$=4 Hz, $H_7$) - 1H at 5.16 ppm (D, J=4 Hz, $H_6$) - 1H at 5.00 ppm et 1H at 4.66 ppm (D, J=13 Hz, $CH_2OCO$) - 1H at 4.16 ppm (M, H piperidine α N equatorial) - 2H at 3.80 ppm (M, $COCH_2N$) - 3H at 3.55 (M, $CH_2S$ et H piperidine α N equatorial) - 1H at 3.05 ppm (M, H piperidine α N axial) - 1H at 2.80 ppm (M, H piperidine α N axial) - 1H at 2.67 ppm (M, H piperidine γ N) - 2H at 1.85 ppm and 2H at 1.50 ppm (M, H piperidine β N) - 6H at 1.44 ppm (2S, $(CH_3)_2C$) - .

NMR n° 24

1H at 9.40 ppm (D, J=9 Hz, CONH) - 2H at 7.85 ppm (D, J=8 Hz, H aromatics ortho $CO_2$) - 3H at 7.70 ppm (S.e., $CH_2N^+H_3$) - 2H at 7.50 ppm (D, J=8 Hz, H aromatics meta $CO_2$) - 1H at 6.70 ppm (S, H thiazole) - 1H at 5.85 ppm (D of D, $J_1$=9 Hz $J_2$=4 Hz, $H_7$) - 1H at 5.25 ppm (D, J=13 Hz, $CH_2OCO$) - 1H at 5.15 ppm (D, J=4 Hz, $H_6$) - 1H at 4.91 ppm (D, J=13 Hz, $CH_2OCO$) - 2H at 3.84 ppm (S, $ArCH_2S$) - 2H at 3.68 ppm (AB, $J_{AB}$=17 Hz, $CH_2S$) - 2H at 2.95 ppm (M, $CH_2$—$N^+H_3$) - 2H at 2.51 ppm (M, $CH_2$—$CH_2N^+H_3$) - 6H at 1.38 ppm (2S, $(CH_3)_2$—C) - .

NMR n° 25

1H at 9.55 ppm (D, J=9 Hz, NHCO) - 1H at 7.80 ppm (S.e., $CH_2NH^+H_3$) - 1H at 6.70 ppm (S, H thiazole) - 1H at 5.76 ppm (D of D, $J_1$=9 Hz $J_2$=4 Hz, $H_7$) - 1H at 5.09 ppm (D, J=4 Hz, $H_6$) - 1 H at 4.95 and 1H at 4.55 ppm (D, J=13 Hz, $CH_2OCO$) - 3H at 3.80 ppm (S, $CH_3ON$) - 2H at 3.50 ppm (AB, $J_{AB}$=17 Hz, $CH_2S$) - 2H at 2.60 ppm (M, $CH_2N^+H_3$) - 1H at 2.25 ppm (M, H cyclohexane γ $CH_2N$) - 9H between 0.8 and 2.0 ppm (M, H cyclohexane) - .

NMR n° 26

1H at 9.56 (D, J=9 Hz, CO NH) - 1H at 8.88 ppm (T, J=7 Hz, Ar $CH_2$ NH CO) - 3H at 8.00 ppm (S.e., $N^+H_3$) - 2H at 7.90 ppm (D, J=8 Hz, H aromatics ortho $CO_2$) - 2H at 7.37 ppm (D, J=8 Hz, H aromatique meta $CO_2$) - 1H at 6.70 ppm (S, H thiazole) - 1H at 5.77 ppm (D of D, $J_1$=9 Hz $J_2$=4 Hz, $H_7$) - 1H at 5.20 ppm (D, J=13 Hz, $CH_2OCO$) - 1H at 5.13 ppm (D, J=4 Hz, $H_6$) - 1H at 4.90 ppm (D, J=13 Hz, $CH_2OCO$) - 2H at 3.41 ppm (D, J=7 Hz, Ar $CH_2$ NH) - 3H at 3.80 ppm (S, $CH_2ON$) - 4H at 3.55 ppm (M, $CH_2NH_3^+$ and $CH_2S$) -

NMR n° 27

1H at 9.56 (D, J=9 Hz, CO NH) - 1H at 8.85 ppm (T, J=7 Hz, Ar $CH_2$ NH CO) - 3H at 7.95 ppm (S.e., $N^+H_3$) - 2H at 7.91 ppm (D, J=8 Hz, H aromatics ortho $CO_2$) - 2H at 7.39 ppm (D, J=8 Hz, H aromatics meta $CO_2$) - 2H at 7.30 ppm (S.e., $NH_2$ thiazole) - 1H at 6.76 ppm (S, H thiazole) - 1H at 5.84 ppm (D of D, $J_1$=9 Hz $J_2$=4 Hz, $H_7$) - 1H at 5.27 ppm (D, J=13 Hz, $CH_2OCO$) - 1H at 5.16 ppm (D, J=4 Hz, $H_6$) - 1H at 4.89 ppm (D, J=13 Hz, $CH_2OCO$) - 2H at 4.40 ppm (D, J=7 Hz, $ArCH_2NHCO$) - 4H at 3.60 ppm (M, $CH_2S$ and $CH_2N^+H_3$) - 6H at 1.41 ppm (2S, $(CH_3)_2C$) - .

NMR n° 28

1H at 9.40 ppm (D, J=9 Hz, CONH)-1H at 8.84 ppm (T, J=7 Hz, Ar $CH_2NH$)-3H at 7.95 ppm (S.e., $NH_3^+$)-2H at 7.85 ppm (M, H aromatics ortho $CO_2$)-2H at 7.51 ppm (M, H aromatics meta et para $CO_2$)-1H at 6.67 ppm (S, H thiazole)-1H at 5.84 ppm (D de D, $J_1$=9 Hz $J_2$=4 Hz, $H_7$)-1H at 5.25 ppm (D, J=13 Hz, $CH_2OCO$)-1H at 5.17 ppm (D, J=4 Hz, $H_6$)-1H at 4.93 ppm (D, J=13 Hz, $CH_2OCO$)-2H at 4.42 ppm (T, J=7 Hz, Ar $CH_2NH$)-4H at 3.60 ppm (M, $Ch_2S$ and $CH_2NH_3$)-6H at 1.41 ppm (2S, $(CH_3)_2C$)-.

NMR n° 29

1H at 9.56 ppm (D, J=9 Hz, CONH)-1H at 8.70 ppm and 1H at 8.42 ppm (S.e., $N^+H_2$ piperidine)-2H at 7.30 ppm (S.e., $NH_2$ thiazole)-1H at 6.65 ppm (S, H thiazole)-1H at 5.76 ppm (D of D, $J_1$=9 Hz $J_2$=4 Hz, $H_7$)-1H at 5.08 ppm (D, J=4 Hz $H_6$)-1H at 4.95 ppm and 1H at 4.71 ppm (D, J=13 Hz, $CH_2OCO$)-3H at 3.79 ppm (S, $CH_3ON$)-2H at 3.55 ppm (AB, $J_{AB}$=17 Hz, $CH_2S$)-2H at 3.20 ppm (M, Hequatoriaux piperidine αNH)-2H 2.90 ppm (M, H axial piperidine αNH)-1H at 2.56 ppm (M, OCO <CH)-2H at 1.95 ppm (H equatorial piperidine βNH)-. 2H at 1.56 ppm (Haxial piperidine βNH) -.

NMR n° 30

1H at 9.58 ppm (D, J=9 Hz, CONH)-1H at 8.85 ppm (T, J=7 Hz, Ar $CH_2$ NHCO) 3H at 8.02 ppm (S.e., $N^+H_3$)-2H at 7.84 ppm (M, H aromatics ortho $CO_2$)-2H at 7.50 ppm (M, H aromatics meta and para $CO_2$)-1H at 6.71 ppm (S, H thiazole)-1H at 5.80 ppm (D de D, $J_1$=9 Hz $J_2$=4 Hz, $H_7$)-1H at 5.24 ppm (D, J=13 Hz, $CH_2O$-CO)-1H at 5.13 ppm (D, J=4 Hz, $H_6$) 1H at 4.92 ppm (D, J=13 Hz, $CH_2OCO$)-2H at 4.37 ppm (D, J=7 Hz, Ar $CH_2NH$)- 3H at 3.82 ppm (S, $CH_3ON$)-4H at 3.60 ppm (M, $CH_2S$ and $CH_2N^+H_3$) -.

NMR n° 31

1H at 9.46 ppm (D, J=9 Hz, CONH)-2H at 7.86 ppm (M, H aromatics ortho $CO_2$)-3H at 7.80 ppm (S.e., $N^+H_3$)-1H at 7.55 ppm (D, J=8 Hz, H aromatic para $CO_2$)-1H at 7.50 ppm (T, J=8 Hz, H aromatic meta $CO_2$)-2H at 7.30 ppm (S.e., $NH_2$ thiazole)-1H at 6.70 ppm (S, H thiazole)-1H at 5.84 ppm (D de D, $J_1$=9 Hz $J_2$=4 Hz, $H_7$)-1H at 5.16 ppm (D, J=4 Hz, $H_6$)-1H at 5.25 ppm and 1H at 4.90 ppm (D, J=13 Hz, $CH_2OCO$)-

2H at 3.62 ppm (AB, $J_{AB}$=17 Hz, $CH_2S$)-3H at 3.02 ppm (M,

Ar—CH—$CH_2$)—6H at 1.40 ppm (2S, $(CH_3)_2$-C)-3H at 1.20 ppm (D, J=7 Hz, $CH_3$—CH—Ar)—

.

NMR n° 32

1H at 9.51 ppm (D, J=9 Hz, CONH)-1H at 7.80 ppm (S.e., $N^+H_3$)-2H at 7.25 ppm (S.e., $NH_2$ thiazole)-1H at 6.70 ppm (S, H thiazole)-1H at 5.84 ppm (D of D, $J_1$=9 Hz $J_2$=4 Hz, $H_7$)-1H at 5.17 ppm (D, J=4 Hz, $H_6$)-1H at 4.97 ppm et 1H at 4.60 ppm (D, J=13 Hz, $CH_2OCO$)-1H at 3.56 ppm et 1H at 3.44 ppm (D, J=17 Hz, $CH_2S$)-2H at 2.56 ppm (M, $CH_2N^+H_3$)-5H at 2.40 ppm (M,

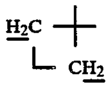

and OCO—<CH)-6H at 1.90 ppm, 1H at 1.45 ppm 2H, at 1.25 ppm and 2H at 0.95 ppm (M,

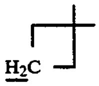

and $CH_2$ and CH cyclohexane).

NMR n° 33

1H at 9.60 ppm (D, J=9 Hz, CONH)-2H at 7.90 ppm (M, H aromatics ortho $CO_2$)-3H at 7.80 ppm (S.e., $N^+H_3$)-1H at 7.55 ppm (D, J=8 Hz, H aromatic para $CO_2$)-1H at 7.50 ppm (T, J=8 Hz, H aromatic meta $CO_2$)-2H at 7.36 ppm (S.e., $NH_2$ thiazole)-1H at 6.71 pp (S, Hthiazole)-1H at 5.79 ppm (D de D, $J_1$=9 Hz $J_2$=4 Hz, $H_7$)-1H at 5.11 ppm (D, J=4 Hz, $H_6$)-1H at 5.25 ppm 1H at 4.95 ppm (D, J=13 Hz, $CH_2OCO$)-3H at 3.80 ppm (S, $H_3CON$)-2H at 3.61 ppm (AB, $J_{AB}$=17 Hz, $CH_2S$)-3H at 3.02 ppm (M, ArCH—$CH_2$)—3H at 1.21 ppm (D, J=7 Hz, $CH_3$—CH—Ar)—

NMR n° 34

1H at 9.60 ppm (D, J=9 Hz, NHCO)-3H at 8.25 ppm (S.e., $N^+H_3$)-1H at 8.05 ppm (S, Haromatic ortho $CO_2$ and ortho $CH_2$)-1H at 7.95 ppm (D, J=8 Hz, H aromatic ortho $CO_2$ and para $CH_2$)-1H at 7.70 ppm (D, J=8 Hz, H aromatic para $CO_2$)-1H at 7.55 ppm (T, J=8 Hz, H aromatic meta $CO_2$)-1H at 6.70 ppm (S, H thiazole)-1H at 5.75 ppm (D de D, $J_1$=9 Hz $J_2$=4 Hz, $H_7$)-1H at 5.20 ppm (D, J=13 Hz, $CH_2OCO$)-1H at 5.10 ppm (D, J=4 Hz, $H_6$)-1H at 4.95 ppm (D, J=13 Hz, $CH_2O$-CO)-2H at 4.10 ppm (M, $CH_2Ar$)-3H at 3.80 ppm (S, $CH_3ON$)-2H at 3.70 ppm (AB, $J_{AB}$=17 Hz, $CH_2$ S)-.

NMR n° 35

1H at 9.58 ppm (D, J=9 Hz, NHCO)-2H at 8.60 ppm (2 S.e., $NH_2^+$ piperidinium)-2H at 7.40 ppm (S.e. $NH_2$ thiazole)-1H at 7.11 ppm (S, H thiazole)-1H at 5.75 ppm (D of D, $J_1$=9 Hz, $J_2$=4 Hz, $H_7$)-1H at 5.10 ppm (D, J=4 Hz, $H_6$)-1H at 5.00 ppm (2 D, J=13 Hz, $CH_2O$-CO)-1H at 4.75 ppm (2 D, J=13 Hz, $CH_2OCO$)-3H at 3.80 ppm (S, $NOCH_3$)-2H at 3.50 ppm (AB, $J_{AB}$=17 Hz, $CH_2S$)-5H between 3.45 and 2.6 ppm (M, $CH_2N$ et $CO_2H$-<CH)-4H between 2.00 and 1.45 ppm (M, $(CH_2)_2$-$CH_2N$)-$CH_2N$)-.

NMR n° 36

1H at 9.56 ppm (2 D, J=9 Hz, NHCO)-7.80 ppm (S.e., $CH_2NH_3^+$)-2H at 7.40 ppm (S.e., $NH_2$ thiazole)-1H at 6.72 ppm (S, H thiazole)-1H at 5.75 ppm (D of D, $J_1$=9 Hz, $J_2$=4 Hz, $H_7$)-1H at 5.09 ppm (D, J=4 Hz, $H_6$)-1H at 5.00 ppm (2 D, J=13 Hz, $CH_2OCO$)-1H at 4.65 ppm (2 D, J=13 Hz, $CH_2OCO$)-3H at 3.83 ppm (S, $NOCH_3$)-1H at 3.54 ppm (2 D, J=17 Hz, $CH_2S$)-1H at 3.45 ppm (2 D, J=17 Hz, $CH_2S$)-3H at 2.83 ppm (M, $CH_2NH_3^+$ et <CH-COOH)-9H between 2.0 and 1.1 ppm (M, $CH_2$ cyclohexane and —CH—$CH_2NH_3^+$)-.

NMR n° 37

1H at 9.61 ppm (D, J=9 Hz, NHCO)-3H at 7.85 ppm (S.e., $CH_2NH_3^+$)-2H at 7.40 ppm (S.e., $NH_2$ thiazole)-1H at 6.71 ppm (S, H thiazole)-1H at 5.79 ppm (D of D, $J_1$=9 Hz, $J_2$=4 Hz, $H_7$)-1H at 5.09 ppm (D, J=4 Hz, $H_6$)-1H at 5.02 ppm (2 D, J=13 Hz, $CH_2OCO$)-1H at 4.56 ppm (2 D, J=13 Hz, $CH_2OCO$)-3H at 3.83 ppm (S, $NOCH_3$)-3H at 3.82 ppm (AB, $J_{AB}$=17 Hz, $CH_2S$)-1H at 3.00 ppm et 1H at 2.87 ppm (2M, $CH_2NH_3^+$)-1H at 2.77 ppm (M, —CH—$CH_3$)—3H at 1.12 ppm (D, J=7 Hz,

—CH—$CH_3$)—

.

NMR n° 38

1H at 9.62 ppm (D, J=9 Hz, CONH)-3H at 7.85 ppm (S.e., >CH—$NH_3^+$)-2H at 7.40 ppm (S.e., $NH_2$ thiazole)-1H at 6.70 ppm (S, H thiazole)-1H at 5.76 ppm (D de D, $J_1$=9 Hz, $J_2$=4 Hz, $H_7$)-1H at 5.08 ppm (D, J=4 Hz, $H_6$)-1H at 4.95 ppm (D, J=13 Hz, $CH_2OCO$)-1H at 4.69 ppm (D, J=13 Hz, $CH_2OCO$)-3H at 3.50 ppm (AB, $J_{AB}$=17 Hz, —$CH_2S$)-1H at 3.00 ppm (M, >CH—$NH_3^+$)-1H at 2.50 ppm (M, >CH—COOH)-1H at 2.10 ppm, 3H at 1.85 ppm et 4H at 1.30 ppm (3M, $CH_2$ cyclohexane)-.

NMR n° 39

1H at 9.40 ppm (D, J=9 Hz, NHCO)-2H at 7.91 ppm (D, J=8 Hz, H aromatics ortho O-CO)-3H at 7.80 ppm (S.e., $CH_2N\underline{H}_3^+$)-2H at 7.45 ppm (D, J=8 Hz, H aromatics meta O—CO)-2H at 7.40 ppm (S.e., $N\underline{H}_2$ thiazole)-1H at 6.70 ppm (S, H thiazole)-1H at 5.81 (D de D, $J_1$=9 Hz, $J_2$=4 Hz, $H_7$)-1H at 5.23 ppm (D, J=13 Hz, $C\underline{H}_2OCO$)-2H at 3.85 ppm (S, $ArC\underline{H}_2S$)-3H at 3.81 ppm (S, $NOCH_3$)-2H at 3.70 ppm (AB, $J_{AB}$=17 Hz, $C\underline{H}_2S$)-2H at 2.95 ppm (M, $C\underline{H}_2NH_3^+$)-2H at 2.55 ppm (T, J=7 Hz, S-$C\underline{H}_2CH_2NH_2$)-.

NMR n° 40

1H at 10.55 ppm (S, $ArN\underline{H}CO$)-1H at 9.61 ppm (D, J=9 Hz, $CON\underline{H}$)-2H at 7.82 ppm (D, J=8 Hz, H aromatics ortho-OCO—)-3H at 7.77 ppm (S.e., $CH_2N\underline{H}_3^+$)-2H at 7.60 ppm (D, J=8 Hz, H aromatics meta-OCO—)-2H at 7.35 ppm (S.e., $N\underline{H}_2$ thiazole)-1H at 6.71 ppm (S, H thiazole)-1H at 5.78 ppm (D of D, $J_1$=9 Hz, $J_2$=4 Hz, $H_7$)-2H at 5.15 ppm (M, $H_6$ and $C\underline{H}_2OCO$)-1H at 4.96 ppm (D, J=13 Hz, $C\underline{H}_2OCO$)-3H at 3.80 ppm (S, $NOC\underline{H}_3$)-2H at 3.60 ppm (AB, $J_{AB}$=17 Hz, $C\underline{H}_2S$)-2H at 3.60 ppm (M, $C\underline{H}_2NH_3^+$)-2H at 2.70 ppm (T, J=7 Hz, $C\underline{H}_2$-$CH_2NH_3^+$)-.

NMR n° 41

1H at 9.60 ppm (D, J=9 Hz, CON$\underline{H}$—)-2H at 8.60 ppm (S.e., $N\underline{H}_2^+$ piperidinium)-2H at 7.40 ppm (S.e., $N\underline{H}_2$ thiazole)-1H at 6.76 ppm (S, H thiazole)-1H at 5.82 ppm (D of D, $J_1$=9 Hz, $J_2$=4 Hz, $H_7$)-1H at 5.15 ppm (D, J=4 Hz, $H_6$)-1H at 5.10 ppm (2D, J=13 Hz, $C\underline{H}_2O$-CO)-1H at 4.76 ppm (2D, J=13 Hz, $C\underline{H}_2OCO$)-3H at 3.88 (N-OC$\underline{H}_3$)-2H at 3.57 ppm (AB, $J_{AB}$=17 Hz, $CH_2S$)-1H at 3.45 ppm (M, H $\alpha NH_2^+$)-1H at 3.26 ppm et 1H at 2.95 ppm (2M, $C\underline{H}_2$ $\alpha NH_2^+$)-2H at 2.70 ppm (M, OCO—$C\underline{H}_2$)-6H between 1.3 and 2 ppm (M, $C\underline{H}_2$ $\beta$ et $\gamma$ $NH_2^+$)-.

NMR n° 42

1H at 9.70 ppm (D, J=9 Hz, CON$\underline{H}$)-1H at 8.60 ppm and 1H at 8.25 ppm (2M, $N\underline{H}_2^+$ piperidinium)-2H at 7.40 ppm (S.e., $N\underline{H}_2$ thiazole)-1H at 6.76 ppm (S, H thiazole)-1H at 5.82 ppm (D of D, $J_1$=9 Hz, $J_2$=4 Hz, $H_7$)-1H at 5.15 ppm (D, J=4 Hz, $H_6$)-1H at 5.02 ppm (D, J=13 Hz, $C\underline{H}_2OCO$)-1H at 4.74 ppm (D, J=13 Hz, $C\underline{H}_2OCO$)-3H at 3.87 ppm (S, $NOCH_3$)-2H at 3.57 ppm (AB, $J_{AB}$=17 Hz, $C\underline{H}_2S$)-2H at 3.25 ppm (M, H equatorial piperidiunm $\alpha$ $NH_2^+$)-2H at 2.90 ppm (M, H axial piperidinium $\alpha NH_2^+$)-2H at 2.35 ppm (D, J=7 Hz, $OCOC\underline{H}_2$—)-1H at 2.00 ppm (M, $OCOCH_2$<C$\underline{H}$)-2H at 1.80 ppm and 2H at 1.40 ppm (2M, $CH_2$ piperidium $\beta NH_2^+$)-.

NMR n° 43

1H at 9.70 ppm (D, J=9 Hz, CON$\underline{H}$)-2H at 9.00 ppm (S.e.,

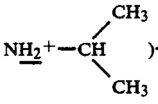 )—2H at 8.05 ppm (D, J=8 Hz, H aromatics ortho OCO)-2H at 65 ppm (D, J=8 Hz, H aromatics meta OCO)-2H at 7.40 ppm (S.e., $N\underline{H}_2$ thiazole)-1H at 6.80 ppm (S, H thiazole)-1H at 5.85 ppm (D of D, $J_1$=9 Hz, $J_2$=4 Hz, $H_7$)-1H at 5.30 ppm (D, J=13 Hz $C\underline{H}_2OCO$)-1H at 5.20 ppm (D, J=4 Hz, $H_6$)-1H at 5.00 ppm (D, J=13 Hz, $C\underline{H}_2OCO$)-2H at 4.27 ppm (M, $ArCH_2NH_2^+$—)-3H at 3.90 ppm (S, $NOC\underline{H}_3$)-2H at 3.75 ppm (AB, $J_{AB}$=17 Hz, $C\underline{H}_2S$)-1H at 3.40 ppm (M, 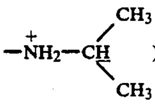 )—6H at 1.30 ppm (D, J=7 Hz,

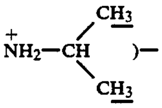 )—

NMR n° 44

1H at 9.20 ppm (D, J=9 Hz, CON$\underline{H}$)-3H at 8.05 ppm (S.e., $ArCH_2N^+H_3$)-2H at 7.40 ppm (S.e., $N\underline{H}_2$ thiazole)-1H at 7.10 ppm (S, H aromatic)-1H at 6.70 ppm (S, H thiazole)-1H at 5.84 ppm (D of D, $J_1$=9 Hz, $J_2$=4 Hz, $H_7$)-2H at 5.20 ppm (M, $H_6$ and $C\underline{H}_2OCO$)-1H at 5.04 ppm (D, J=13 Hz, $C\underline{H}_2OCO$)-2H at 4.10 ppm (M, $ArC\underline{H}_2N^+H_3$)-3H at 3.80 ppm (S, $NOC\underline{H}_3$)-2H at 3.60 ppm (AB, $J_{AB}$=17 Hz, $C\underline{H}_2S$)-3H at 1.40 ppm, 3H at 1.30 ppm and 3H at 1.20 ppm (3S, $C\underline{H}_3Ar$)-.

NMR n° 45

1H at 9.70 ppm (D, J=9 Hz, CON$\underline{H}$)-3H at 8.15 ppm (S.e., $N\underline{H}_3^+$)-2H at 7.40 ppm (S.e., $N\underline{H}_2$ thiazole)-2H at 7.40 ppm and 2H at 7.00 ppm (2D, J=8 Hz, H aromatics)-1H at 6.80 ppm (S, H thiazole)-1H at 5.82 ppm (D of D, $J_1$=9 Hz, $J_2$=4 Hz, $H_7$)-1H at 5.15 ppm (D, J=4 Hz, $H_6$)-1H at 5.12 ppm (D, J=13 Hz, $C\underline{H}_2OCO$)-2H at 4.86 ppm (S, $C\underline{H}_2OAr$)-1H at 4.82 ppm (D, J=13 Hz, $C\underline{H}_2OCO$)-2H at 4.00 ppm (M, $ArC\underline{H}_2N^+H_3$)-3H at 3.85 ppm (S, $NOC\underline{H}_3$)-2H at 3.55 ppm (AB, $J_{AB}$=17 Hz, $C\underline{H}_2S$)-.

NMR n° 46

1H at 9.58 ppm (D, J=9 Hz, CON$\underline{H}$)-3H at 7.90 ppm (S.e.,

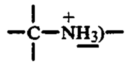

2H at 7.40 ppm (S.e., $N\underline{H}_2$ thiazole)-1H at 6.70 ppm (S, H thiazole)-1H at 5.82 ppm (D of D, $J_1$=9 Hz, $J_2$=4 Hz, $H_7$ )-1H at 5.10 ppm (D, J=4 Hz, $H_6$)-1H at 5.05 ppm (D, J=13 Hz, $C\underline{H}_2OCO$)-1H at 4.70 ppm (D, J=13 Hz, $C\underline{H}_2OCO$)-3H at 3.80 ppm (S, N-OC$\underline{H}_3$)-2H at 3.55 ppm (AB, $J_{AB}$=17 Hz, $C\underline{H}_2S$)-2H at 2.95 ppm (M, $C\underline{H}_2N^+H_3$)-6H at 1.16 ppm (S, 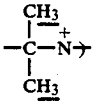

NMR n° 47

1H at 9.00 ppm (D, J=9 Hz, CON$\underline{H}$)-3H at 8.05 ppm (S.e., $CH_2N^+\underline{H}_3$)-2H at 8.00 ppm (D, J=8 Hz, H aromatics ortho OCO)-2H at 7.50 ppm (D, J=8 Hz, H aromatics meta OCO)-2H at 7.30 ppm (S.e., $N\underline{H}_2$ thiazole)-1H at 6.71 ppm (S, H thiazole)-1H at 5.80 ppm (Dof D, $J_1=9$ Hz, $J_2=4$ Hz, $H_7$)-1H at 5.25 ppm (D, J=13 Hz, $CH_2OCO$)-1H at 5.10 ppm (D, J=4 Hz, $H_6$)-1H at 4.95 ppm (D, J=13 Hz, $CH_2OCO$)-3H at 3.82 ppm (S, $NOCH_3$)-2H at 3.66 ppm (AB, $J_{AB}=17$ Hz, $CH_2S$)-2H at 3.55 ppm (S.e., $CH_2N^+H_3$)-3H at 3.23 ppm (S,

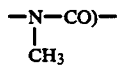

NMR n° 48

1H at 9.46 ppm (D, J=9 Hz CONH)-1H at 8.51 ppm (S, H thiazole ester)-3H at 7.90 ppm (S.e., $CH_2N^+H_3$)-2H at 7.45 ppm (S.e., $NH_2$ thiazole)-1H at 6.69 ppm (s, H thiazole)-1H at 5.82 ppm (D de D, $J_1=9$ Hz, $J_2=4$ Hz, $H_7$)-2H at 5.20 ppm (M, $H_6$ and $CH_2OCO$)-1H at 4.96 ppm (D, J=13 Hz, $CH_2OCO$)-2H at 3.60 ppm (AB, $J_{AB}=17$ Hz, $CH_2$ S)-4H at 3.25 ppm (M, $CH_2$—$CH_2NH^+{}_3$)-6H at 1.42 ppm (2S,

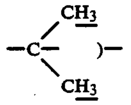

NMR n° 49

1H at 9.60 ppm (D, J=9 Hz, CONH)-1H at 8.50 ppm (S, H thiazole ester)-3H at 7.85 ppm (S.e., $CH_2N^+H_3$)-2H at 7.30 ppm (S.e., $NH_2$ thiazole)-1H at 6.71 ppm (S, H thiazole)-1H at 5.78 ppm (D of D, $J_1=9$ Hz, $J_2=4$ Hz, $H_7$)-1H at 5.19 ppm (D, J=13 Hz, $CH_2OCO$)-1H at 5.14 ppm (D, J=4 Hz, $H_6$)-1H at 4.92 ppm (D, J=13 Hz, $CH_2OCO$)-3H at 3.81 ppm (S, $NOCH_3$)-2H at 3.61 ppm (AB, $J_{AB}=17$ Hz, $CH_2S$)-4H at 3.26 ppm (M, $CH_2CH_2N^+H_3$)-.

NMR n° 50

1H at 9.46 ppm (D, J=9 Hz, CONH)-1H at 8.50 ppm (S, H thiazole ester)-3H at 7.80 ppm (S.e., $CH_2N^+H_3$)-2H at 7.40 ppm (S.e., $NH_2$ thiazole)-1H at 6.68 ppm (S, H thiazole)-1H at 5.80 ppm (D of D, $J_1=9$ Hz, $J_2=4$ Hz, $H_7$)-2H at 5.20 ppm (M, $H_6$ and $CH_2OCO$)-1H at 4.86 ppm (D, J=13 Hz, $CH_2OCO$)-2H at 3.66 ppm (AB, $J_{AB}=17$ Hz, $CH_2S$)-2H at 3.00 ppm (T, J=7 Hz, $CH_2CH_2CH_2N^+H_3$)-2H at 2.84 ppm (M, —$CH_2N^+H_3$)-2H at 1.96 ppm (M, $CH_2CH_2CH_2N^+H_3$)-6H at 1.36 ppm (2S,

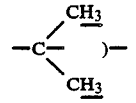

NMR n° 51

1H at 9.46 ppm (D, J=9 Hz, CONH)-1H at 8.50 ppm (S, H thiazole ester)-3H at 7.80 ppm (S.e., $CH_2N^+H_3$)-2H at 7.40 ppm (S.e., $NH_2$ thiazole)-1H at 6.68 ppm (S, H thiazole)-1H at 5.80 ppm (D of D, $J_1=9$ Hz, $J_2=4$ Hz, $H_7$)-2H at 5.20 ppm (M, $H_6$ and $CH_2OCO$)-1H at 4.96 ppm (D, J=13 Hz, $CH_2OCO$)-3H at 3.81 ppm (S, $NOCH_3$)-2H at 3.66 ppm (AB, $J_{AB}=17$ Hz, $CH_2S$)-2H at 3.08 ppm (T, J=7 Hz, —$CH_2CH_2CH_2N^+H_3$)-2H at 2.84 ppm (M, $CH_2N^+H_3$)-2H at 1.96 ppm (M, $CH_2CH_2CH_2N^+H_3$)-.

NMR n° 52

1H at 9.60 ppm (D, J=9 Hz, CONH)-1H at 8.60 ppm (S, H thiazole ester)-3H at 8.50 ppm (S.e., $CH_2N^+H_3$)-2H at 7.40 ppm (S.e., $NH_2$ thiazole)-1H at 6.70 ppm (S, H thiazole)-1H at 5.80 ppm (D of D, $J_1=9$ Hz, $J_2=4$ Hz, $H_7$)-2H at 5.15 ppm (M, $H_6$ and $CH_2OCO$)-1H at 4.96 ppm (D, J=13 Hz, $CH_2OCO$)-2H at 4.45 ppm (S.e., $CH_2N^+H_3$)-3H at 3.78 ppm (S, $NOCH_3$)-2H at 3.57 ppm (AB, $J_{AB}=17$ Hz, $CH_2S$)-.

NMR n° 53

1H at 9.70 ppm (D, J=9 Hz, CONH)-1H 8.70 ppm and 1H at 8.40 ppm (2M, $N^+H_2$ piperidinium)-2H at 7.80 ppm (S.e., $NH_2$ thiazole)-1H at 6.80 ppm (S, H thiazole)-1H at 5.85 ppm (D of D, $J_1=9$ Hz, $J_2=4$ Hz, $H_7$)-1H at 5.20 ppm (D, J=4 Hz, $H_6$)-1H at 5.00 ppm (D, J=13 Hz, $CH_2OCO$)-1H at 4.72 ppm (D, J=13 Hz, $CH_2OCO$)-2H at 3.90 ppm (D, J=7 Hz, $NOCH_2$—)-2H at 3.55 ppm (AB, $J_{AB}=17$ Hz, $CH_2S$)-2H at 3.25 ppm (M, H equatorial $\alpha$ $N^+H_2$ piperidinium)-2H at 2.90 ppm (M, H axial $N^+H_2$ piperidinium)-2H at 2.35 ppm (D, J=7 Hz, $OCOCH_2$)-3H at 2.00 ppm and 3H at 1.20 ppm (M, $CH_2$ $\beta N^+H_2$, $OCOCH_2$—<CH et CH cyclopropyl)-2H at 0.50 ppm and 2H at 0.30 ppm (2M, $CH_2$ cyclopropane)-.

NMR n° 54

1H at 9.55 ppm (D, J=9 Hz, CONH)-3H at 7.70 ppm (S.e., $CH_2N^+H_3$)-2H at 7.25 ppm (S.e., $NH_2$ thiazole)-1H at 6.72 ppm (S, H thiazole)-1H at 5.75 ppm (D of D, $J_1=9$ Hz, $J_2=4$ Hz, $H_7$)-1H at 5.08 ppm (D, J=4 Hz, $H_6$)-1H at 4.95 ppm (D, J=13 Hz, $CH_2OCO$)-1H at 4.66 ppm (D, J=13 Hz, $CH_2OCO$)-3H at 3.81 ppm (S, $NOCH_3$)-2H at 3.49 ppm (AB, $J_{AB}=17$ Hz, $CH_2S$)-2H at 2.70 ppm (M, $CH_2N^+H_3$)-2H at 2.30 ppm (T, J=7 Hz, $CH_2$—$(CH_2)_4$ $NH_2$)-4H at 1.50 ppm (M, —$CH_2$—$CH_2CH_2$—$CH_2$—$CH_2N^+H_3$)-2H at 1.20 ppm (M, —$(CH_2)_2$—$CH_2$—$(CH_2)_2N^+H_3$)-.

NMR n° 55

1H at 9.62 ppm(D, J=9 Hz, CONH)-3H at 7.80 ppm (S.e., $CH_2N^+H_3$)-2H at 7.55 ppm (S.e., $NH_2$ thiazole)-1H at 6.76 ppm (S, H thiazole)-1H at 5.80 ppm (D of D, $J_1=9$ Hz, $J_2=4$ Hz, $H_7$)-1H at 5.15 ppm (D, J=4 Hz, $H_6$)-1H at 5.10 ppm (D, J=13 Hz, $CH_2OCO$)-1H at 4.70 ppm (D, J=13 Hz, $CH_2OCO$)-3H at 3.85 ppm (S, N-$OCH_3$)-2H at 3.52 ppm (AB, $J_{AB}=17$ Hz, $CH_2S$)-2H at 2.80 ppm (M, $CH_2N^+H_3$)-2H at 2.35 ppm (T, J=7 Hz, $OCOCH_2$)-4H at 1.51 ppm and 6H at 1.26 ppm (2M, $OCOCH_2(CH_2)_5$—$CH_2N^+H_3$)-.

NMR n° 56

1H at 9.56 ppm (D, J=9 Hz, CONH)-2H at 8.30 and 8.55 ppm (2M, $N^+H_2$ piperidinium)-2H at 7.40 ppm (S.e., $NH_2$ thiazole)-1H at 6.69 pm (S, H thiazole)-1H at 5.74 ppm (D of D, $J_1=9$ Hz, $J_2=4$ Hz, $H_7$)-1H at 5.10 ppm (D, J=4 Hz, $H_6$)-1H at 4.96 ppm (2D, J=13 Hz, $CH_2OCO$)-1H at 4.66 ppm (D, J=13 Hz, $CH_2OCO$)-3H at 3.80 ppm (S, $NOCH_3$)-2H at 3.49 ppm (AB, $J_{AB}=17$ Hz, $CH_2S$)-2H at 3.15 ppm (M, H equatorital $\alpha N^+H_2$ piperidinium)-1H at 2.75 ppm et 1H at 2.55 ppm (2M, H axial $\alpha N^+H_2$ piperidinium)-2H at 2.36 ppm (T, J=7 Hz, $OCOCH_2$—)-7H between 1 and 2 ppm (M, $OCOCH_2CH_2$- and 5H piperidinium)-.

NMR n° 57

1H at 9.45 ppm (D, J=9 Hz, CONH)-1H at 8.55 ppm and 1H at 8.40 ppm (2M, $N^+H_2$ piperidinium)-2H at 7.40 ppm(S.e., $NH_2$ thiazole)-1H at 6.69 ppm (S, H thiazole)-1H at 5.84 ppm (D of D, $J_1$=9 Hz, $J_2$=4 Hz, $H_7$)-1H at 5.13 ppm (D, J=4 Hz, $H_6$)-1H at 4.97 ppm (2D, J=13 Hz, $CH_2OCO$)-1H at 4.66 ppm (D, J=13 Hz, $CH_2OCO$)-2H at 3.51 ppm (AB, $J_{AB}$=17 Hz, $CH_2S$)-2H at 3.16 ppm (M, H équatoriaux $\alpha N^+H_2$ piperidinium)-1H at 2.75 ppm and 1H at 2.55 ppm (2M, H axial $\alpha N^+H_2$ piperidinium)-2H at 2.36 ppm (T, J=7 Hz, $OCOCH_2$—)-6H at 1.42 ppm (2S,

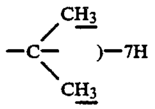

between 1 and 2 ppm (M, $OCOCH_2CH_2$, 5H piperidinium)-.

NMR n° 58

1H at 9.60 ppm (D, J=9 Hz, CONH)-1H at 8.55 ppm et 1H at 8.26 ppm (2 M.e., $N^+H_2$ piperidinium)-2H at 7.50 ppm (S.e., $NH_2$ thiazole)-1H at 6.70 ppm (S, H thiazole)-1H at 5.75 ppm (D of D, $J_1$=9 Hz, $J_2$=4 Hz, $H_7$)-1H at 5.10 ppm (D, J=4 Hz, $H_6$)-1H at 4.96 ppm (D, J=13 Hz, $CH_2OCO$)-1H at 4.66 ppm (D, J=13 Hz, $CH_2OCO$)-3H at 3.82 ppm (s, $NOCH_3$)-2H at 3.50 ppm (AB, $J_{AB}$=17 Hz, $CH_2S$)-2H at 3.20 ppm (M, H equatorial $\alpha N^+H_2$ piperidinium)-2H at 2.80 ppm (M, H axial $\alpha N^+H_2$ piperidinium)-2H at 2.38 ppm ( T, J=7 Hz, $OCOCH_2$)-2H at 1.70, 3H at 1.48 et 2H at 1.20 ppm (3M, $CH_2$ $\beta N^+H_2$ piperidinium, —<CHpiperidinium et $OCOCH_2CH_2$)-.

NMR n° 59

1H at 9.45 ppm (D, J=9 Hz, CONH)-1H at 8.50 ppm et 1H at 8.20 ppm (2 M.e., $N^+H_2$ piperidinium)-2H at 7.50 ppm (S.e., $NH_2$ thiazole)-1H at 6.71 ppm (S, H thiazole)-1H at 5.84 ppm (D of D, $J_1$=9 Hz, $J_2$=4 Hz, $H_7$)-1H at 5.11 ppm (D, J=4 Hz, $H_6$)-1H at 4.96 ppm (D, J=13 Hz, $CH_2OCO$)-1H at 4.67 ppm (D, J=13 Hz, $CH_2OCO$)-2H at 3.52 ppm (AB, $J_{AB}$=17 Hz, $CH_2S$)-2H at 3.24 ppm (M, H equatorial $\alpha N^+H_2$ piperidinium)-2H at 2.77 ppm (M, H axial $\alpha N^+H_2$ piperidinium)-2H at 2.42 ppm (T, J=7 Hz, $OCOCH_2$—)-2H at 1.70, 3H at 1.40 and 2H at 1.20 ppm (3M, $CH_2\beta N^+H_2$ piperidinium, —<$CH^2$ piperidinium and $OCOCH_2CH_2$)-6H at 1.42 ppm

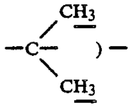

NMR n° 60

1H at 9.47 ppm (D, J=9 Hz, CONH)-2H at 8.80 ppm (M, $N^+H_2$ decahydroquinoleinium)-2 H at 7.60 ppm (S.e., $NH_2$ thiazole)-1H at 6.71 ppm (S, H thiazole)-1H at 5.84 ppm (D of D, $J_1$=9 Hz, $J_2$=4 Hz, $H_7$)-1H at 5.12 ppm (D, J=4 Hz, $H_6$)-1H at 5.06 ppm (2D, J=13 Hz, $CH_2OCO$)-1H at 4.72 ppm (D, J=13 Hz, $CH_2OCO$)-2H at 3.55 ppm (AB, $J_{AB}$=17 Hz, $CH_2S$)-1H at 3.40 ppm (M, $H\alpha N^+H_2$ cycle junction)-1H at 3.20 ppm (M, H equatorial $\alpha N^+H_2$ decahydroquinoleinium)-1H at 3.00 ppm (M, H axial $\alpha N^+H_2$ decahydroquinoleinium)-1H at 2.80 ppm (M, OCO—<CH)-6H at 1.42 ppm (2S,

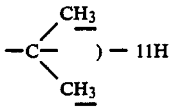

between 1 and 2.05 ppm (M, H decahydroquinoleinium)-.

NMR n° 61

1H at 9.60 ppm (D, J=9 Hz, CONH)-1H at 8.80 ppm (T, J=7 Hz, ArCONH)-2H at 8.00 ppm (D, J=8 Hz, H aromatic)-2H at 7.90 ppm (D, J=8 Hz, H aromatic)-3H at 7.75 ppm (S.e., $CH_2N^+H_3$)-2H at 7.30 ppm (S.e., $NH_2$ thiazole)-1H at 6.71 ppm (S, H thiazole)-1H at 5.79 ppm (D of D, $J_1$=9 Hz, $J_2$=4 Hz, $H_7$)-1H at 5.24 ppm (D, J=13 Hz, $CH_2OCO$)-1H at 5.12 ppm (D, J=4 Hz, $H_6$)-1H at 4.94 ppm (D, J=13 Hz, $CH_2OCO$)-3H at 3.80 ppm (S, $NOCH_3$)-2H at 3.68 ppm (AB, $J_{AB}$=17 hz, $CH_2S$)-2H at 3.50 ppm (M, $CH_2N^+H_3$)-2H at 2.95 ppm (M, $CH_2CH_2N^+H_3$)-.

NMR n° 62

1H at 9.45 pp (D, J=9 Hz, CONH)-1H at 8.80 ppm (T, J=7 Hz, ArCONH)-2H at 8.00 ppm (D, J=8 Hz, H aromatic)-2H at 7.90 ppm (D, J=8 Hz, H aromatics)-3H at 7.80 ppm (S.e., $CH_2N^+H_3$)-2H at 7.40 ppm (S.e., $NH_2$ thiazole)-1H at 6.70 ppm (S, H thiazole)-1H at 5.84 ppm (D of D, $J_1$=9 Hz, $J_2$=4 Hz, $H_7$)-1H at 5.25 ppm (D, J=13 Hz, $CH_2OCO$)-1H at 5.15 ppm (D, J=4 Hz, $H_6$)-1H at 4.95 ppm (D, J=13 Hz, $CH_2OCO$)-2H at 3.69 ppm (AB, $J_{AB}$=17 Hz, $CH_2S$)-2H at 3.50 ppm (M, $CH_2N^+H_3$)-2H at 2.98 ppm (M, $CH_2$—$CH_2N^+H_3$)-6H at 1.41 ppm (2S,

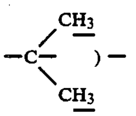

EXAMPLE 64

7-[2-(2-amino 4-thiazolyl) 2-(2-carboxy 2-propyl oxyimino) acetamido]3-[(2-methyl 4-aminomethyl benzoyl)thiomethyl] 3-cepheme 4-carboxylic acide bis trifluoracetate syn isomer (SR 42943)

(I) $R_1=R_2=CH_3$ $R_3$=COOH X=S n=0

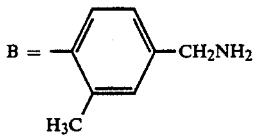

(a) 2-methyl 4-tertiobutoxycarbonylaminomethyl thiobenzoic acid.

2.65 g of 2-methyl 4-tertiobutoxycarbonylaminomethyl thiobenzoic acid and 1.4 ml of triethylamine are dissolved in 60 ml of methylene chloride. The solution is cooled to 4° C. then 1.3 ml of isobutyl chloroformiate are added and the mixture is stirred for 15 minutes. Keeping the temperature to 4° C., a current of hydrogen sulfide is bubbled through the solution and 1.5 ml of triethylamine are added. After 15 minutes, the current of hydrogen sulfide is stopped and stirring continues for 15 minutes, still at 4° C. The solvent is evaporated in vacuo and the residual is taken up in methylene chloride and the sulfate buffer pH2. The organic phase is separated and the aqueous phase is re-extracted with methylene chloride. The organic phases are re-grouped, dried over magnesium sulfate and evaporated to dryness. The residual is taken up in 40 ml of acetone and the solution is used as is in the next step.

(b) 7-[2-(2-tritylamino 4-thiazolyl) 2-(2-tertiobutoxycarbonyl 2-propyl oxyimino acetamido] 3-[(2-methyl 4-tertiobutoxycarbonylaminomethyl benzoyl) thiomethyl] 3-cepheme 4-carboxylate of teriobutyl 1 β-S-oxide syn isomer.

A mixture of 2 g of 7-[2-(2-tritylamino 4-thiazolyl) 2-(2-tertiobutoxycarbonyl 2-propyl oxyimino) acetamido] 3-bromomethyl 3-cepheme carboxylate of 4-tertiobutyl 1μ-S-oxide syn isomer, 1 g of sodium iodide and 3 g of potassium bicarbonate in 21 ml of the acetonic thioacide solution prepared above, is stirred for 3 hours at ambient temperature.

The solvent is evaporated to dryness and the residual is taken up in water and methylene chloride. The organic phase is separated, dried over magnesium sulfate and evaporated to dryness.

The product obtained is chromatographed on a column of silica H. The expected product is obtained by eluting with the mixture methylene chloride-methanol: 100-0.7 (vol/vol).

(c) 7-[2-(2-tritylamino 4-thiazolyl) 2-(2-tertiobutoxycarbonyl 2-propyl oxyimino) acetamido] 3-[(2-methyl 4-tertiobutoxycarbonylaminomethyl benzoyl) thiomethyl] 3-cepheme 4-carboxylate of tertiobutyl syn isomer.

Reduction of the S-oxide is carried out with phosphorous tribromide, as indicated in Example 1b.

The resulting product is purified by chromatography on silica H by eluting with the mixture methylene chloride-ethyl acetate 95-5 (vol/vol).

(d) SR 42943.

Using the product obtained above, deprotection is carried out as indicated in Example 1c.

The expected product is isolated in the same way.

NMR Spectrum 1H at 9.40 ppm (D, J=9 Hz, CO NH)-3H at 8.20 ppm (S.e., Ar $CH_2N^+H_3$)-1H at 7.80 ppm (D, J=8 Hz, H aromatic ortho OCS)-2H at 7.40 ppm (M, H aromatics meta OCS)-1H at 6.70 ppm (S, H thiazole)-1H at 5.80 ppm (D of D, $J_1$=9 Hz $J_2$=4 Hz, $H_7$)-1H at 5.10 ppm (D, J=4 Hz, $H_6$)-1H at 4.20 ppm (D, J=13 Hz, $CH_2SCO$)-2H at 4.00 ppm (M, Ar $CH_2$ $N^+H_3$)-1H at 3.95 ppm (D, J=13 Hz, $CH_2SCO$)-1H at 3.75 ppm et 1H at 3.40 ppm (D, J=17 Hz, $CH_2S$)-1H at 2.37 ppm (S, Ar $CH_3$)-6H at 1.42 ppm (2S, $(CH_3)_2$—C)-.

EXAMPLES 65 to 84

The compounds according to the invention are prepared according to the method used in Example 64, they are isolated in trifluoracetate form, and described in Table II, hereafter.

TABLE II

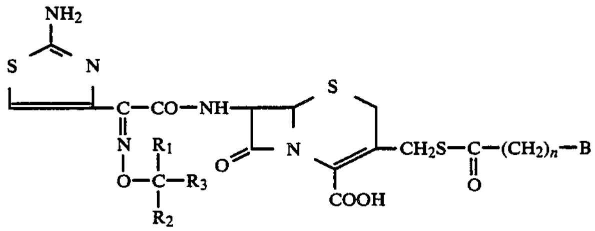

| SR No. | n | $R_1$ | $R_2$ | $R_3$ | B | IR Spectrum Intermediate 3 γCO $cm^{-1}$ | NMR Spectrum |
|---|---|---|---|---|---|---|---|
| 42 887 | 0 | H | H | H | 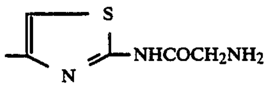 | 1790-1710 1685 ($CH_2Cl_2$) | 63 |
| 42 936 | 0 | H | H | H | 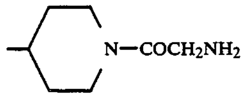 | 1785-1700 1650 | 64 |
| 42 878 | 0 | $CH_3$ | $CH_3$ | COOH | 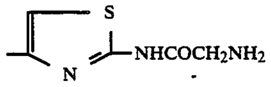 | 1790-1720 1685 | 65 |
| 42 935 | 0 | $CH_3$ | $CH_3$ | COOH | 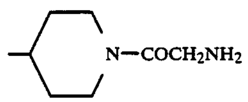 | 1790-1715 1655 ($CH_2Cl_2$) | 66 |

TABLE II-continued
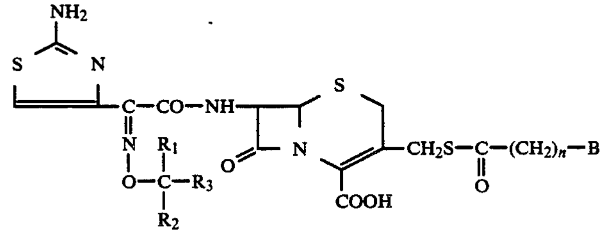
| SR No. | n | R1 | R2 | R3 | B | IR Spectrum Intermediate 3 γCO $cm^{-1}$ | NMR Spectrum |
|---|---|---|---|---|---|---|---|
| 42 944 | 0 | $CH_3$ | $CH_3$ | COOH | 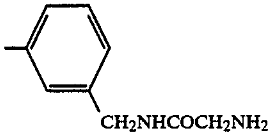 | 1790-1720 | 67 |
| 42 967 | 0 | H | H | H | 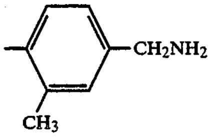 | 1785-1710 | 68 |
| 42 969 | 0 | H | H | H | 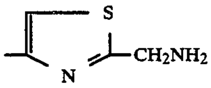 | 1785-1710<br>1675 | 69 |
| 42 973 | 0 | H | H | H | 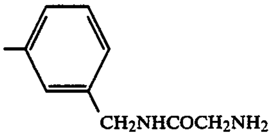 | 1785-1715<br>1670 | 70 |
| 42 975 | 0 | H | H | H | 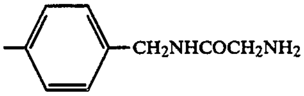 | 1785-1715<br>1670 | 71 |
| 43 014 | 0 | $CH_3$ | $CH_3$ | COOH | 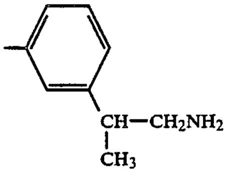 | 1790-1715 | 72 |
| 43 015 | 0 | $CH_3$ | $CH_3$ | COOH | 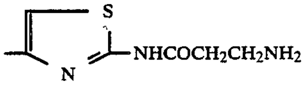 | 1790-1715<br>1685 | 73 |
| 43 025 | 0 | H | H | H | 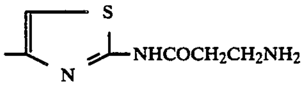 | 1790-1710<br>1675 | 74 |
| 43 031 | 0 | H | H | H | 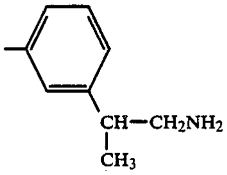 | 1785-1710 | 75 |

TABLE II-continued

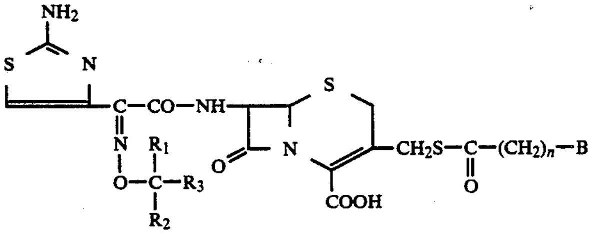

| SR No. | n | $R_1$ | $R_2$ | $R_3$ | B | IR Spectrum Intermediate 3 γCO $cm^{-1}$ | NMR Spectrum |
|---|---|---|---|---|---|---|---|
| 43 027 | 0 | H | H | H | 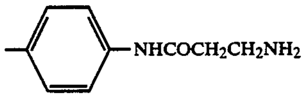 | 1790–1685 | 76 |
| 43 191 | 0 | H | H | H | 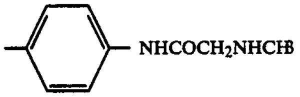 | 1785–1710 1675 | 77 |
| 43 192 | 0 | $CH_3$ . | $CH_3$ | COOH | 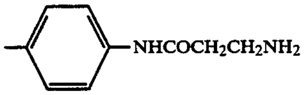 | 1790–1700 | 78 |
| 43 193 | 0 | $CH_3$ | $CH_3$ | COOH | 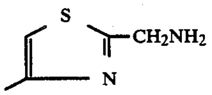 | 1790–1720 | 79 |
| 43 234 | 1 | H | H | H | 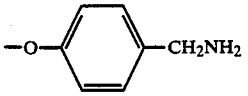 | | 80 |
| 43 235 | 1 | $CH_3$ | $CH_3$ | COOH | 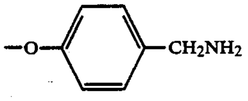 | | 81 |
| 43 525 | 0 | H | H | 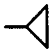 | 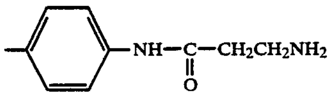 | 1785–1680 | 82 |

NMR n° 63

1H at 12.73 ppm (S, thiazole-NH CO)-4H at 8.30 ppm (S.e., $CH_2NH^+{}_3$ and NH CO)-1H at 8.10 ppm (S, H thiazole thioester)-2H at 7.25 ppm (S.e., $NH_2$ thiazole)-1H at 6.69 ppm (S, H thiazole amine)-1H at 5.70 ppm (D of D, $J_1=9$ Hz $J_2=4$ Hz, $H_7$)-1H at 5.07 ppm (D, J=4 Hz, $H_6$)-1H at 4.20 ppm (D, J=13 Hz, $CH_2SCO$)-3H at 3.90 ppm (M, $CH_2SCO$ and $NHCOCH_2N^+$)-3H at 3.80 ppm (S, $CH_3ON$)-1H at 3.67 ppm and 1H at 3.34 ppm (D, J=17 Hz, $CH_2S$)-.

NMR n° 64

1H at 9.55 ppm (D, J=9 Hz, NHCO)-3H at 8.00 ppm (S.e., $N^+H_3$)-2H at 7.30 ppm (S.e., $NH_2$ thiazole)-1H at 6.71 ppm (S, H thiazole). 1H at 5.73 ppm (D of D, $J_1=9$ Hz $J_2=4$ Hz, $H_7$)-1H at 5.10 ppm (D, J=4 Hz, $H_6$)-1H at 4.30 ppm (M, H piperidine α N equatorial)-4H at 3.90 ppm (M, $CH_2SCO$ et $COCH_2N^+H_3$)-3H at 3.80 ppm (S, $CH_3ON$)-2H at 3.60 ppm (M, H piperidine α N equatorial and $CH_2S$)-1H at 3.25 ppm (D, J=17 Hz, $CH_2S$)-1H at 3.05 ppm (M, H piperidine α N axial)-1H at 2.90 ppm (M, S—CO—<CH)-1H at 2.75 ppm (M, H piperidine α N axial)-4H between 1.3 and 2 ppm (M, H piperidine β N)-.

NMR n° 65

1H at 12.69 ppm (S, thiazole-NH-CO)-1H at 9.42 ppm (D, J=9 Hz, CO NH)-3H at 8.30 ppm (S.e., $N^+H_3$)-1H at 8.10 ppm (S, H thiazole thioester)-2H at 7.30 ppm (S.e., $NH_2$ thiazole)-1H at 6.70 ppm (S, H thiazole amine)-1H at 5.76 ppm (D of D, $J_1=9$ Hz $J_2=4$ Hz, $H_7$)-1H at 5.11 ppm (D, J=4 Hz, $H_6$)-1H at 4.25 ppm (D, J=13 Hz, $CH_2SCO$)-2H at 3.87 ppm (M, $COCH_2N^+$)-1H at 3.83 ppm (D, J=13 Hz, $CH_2SCO$)-1H at 3.67 ppm and 1H at 3.34 ppm (D, J=17 Hz, $CH_2S$)-6H at 1.40 ppm (2S, $(CH_3)_2C$)-.

NMR n° 66

1H at 9.42 ppm (D, J=9 Hz, NHCO)-3H at 8.00 ppm (S.e., $N^+H_3$)-2H at 7.30 ppm (S.e., $NH_2$ thiazole)-1H at 6.66 ppm (S, H thiazole)-1H at 5.75 ppm (D of D, $J_1$=9 Hz $J_2$=4 Hz, $H_7$)-1H at 5.07 ppm (D, J=4 Hz, $H_6$)-1H at 4.20 ppm (M, H piperidine α N equatorial)-1H at 4.00 ppm (D, J=13 Hz, $CH_2SCO$)-2H at 3.80 ppm (M, CO—$CH_2N^+$)-1H at 3.70 ppm (D, J=13 Hz, $CH_2SCO$)-2H at 3.60 ppm (M, H piperidine α N equatorial and $CH_2S$)-2h at 3.27 ppm (D, J=17 Hz, $CH_2S$)-1H at 3.00 ppm (M, H piperidine α N axial)-1H at 2.90 ppm (M, S—CO <H)-1H at 2.75 ppm (M, H piperidine α N axial)-4H between 1.5 and 2 ppm (M, H piperidine β N)-6H at 1.40 ppm (2S, $(CH_3)_2C$)-.

NMR n° 67

1H at 9.40 ppm (D, J329 Hz, NHCO)-1H at 8.85 ppm (T, J=7 Hz, Ar $CH_2$ NH CO)-3H at 8.00 ppm (S.e, $N^+H_3$)-2H at 7.81 ppm (M, H aromatics ortho COS)-2H at 7.50 ppm (M, H aromatics meta, para COS)-1H at 6.66 ppm (S, H thiazole)-1H at 5.80 ppm (D of D, $J_1$=13 Hz $J_2$=4 Hz, $H_7$)-1H at 5.10 ppm (D, J=4 Hz, $H_6$)-2H at 4.39 ppm (D, J=7 Hz, Ar $CH_2$ NH CO)-1H at 4.27 ppm and 1H at 3.94 ppm (D, J=13 Hz, $CH_2SCO$)-1H at 3.66 ppm (D, J=17 Hz, $CH_2S$)-2H at 3.55 ppm (M, $CH_2NHCO$)-1H at 3.37 ppm (D, J=17 Hz, $CH_2S$)-6H at 1.40 ppm (2S, $(CH_3)_2C$)-.

NMR n° 68

1H at 9.54 ppm (D, J=9 Hz, NHCO)-3H at 8.24 ppm (S.e., Ar $CH_2$ $N^+H_3$)-1H at 7.77 ppm (D, J=8 Hz, H aromatic ortho COS)-2H at 7.39 ppm (M, H aromatics meta COS)-2H at 7.27 ppm (S.e., $NH_2$ thiazole)-1H at 6.71 ppm (S, H thiazole)-1H at 5.75 ppm (D of D, $J_1$=9 Hz $J_2$=4 Hz, $H_7$)-1H at 5.09 ppm (D, J=4 Hz, $H_6$)-1H at 4.21 ppm (D, J=13 Hz, $CH_2SCO$)-2H at 4.03 ppm (M, Ar $CH_2$ $N^+$)-1H at 3.92 ppm (D, J=13 Hz, $CH_2SCO$)-3H at 3.79 ppm (S, $CH_3ON$)-1H at 3.71 ppm at 1H at 3.37 ppm (D, J=17 Hz, $CH_2S$)-3H at 2.37 ppm (S, $CH_3$-Ar)-.

NMR n° 69

1H at 9.53 ppm (D, J=9 Hz, NHCO)-1H at 8.57 ppm (S, H thiazole ester)-3H at 8.55 ppm (S.e., $CH_2N^+H_3$)-2H at 7.30 ppm (S.e, $NH_2$ thiazole)-1H at 6.71 ppm (S, H thiazole amine)-1H at 5.71 ppm (D, $J_1$=9 Hz $J_2$=4 Hz, $H_7$)-1H at 5.09 ppm (D, J=4 Hz, $H_6$)-2H at 4.45 ppm (S.e., thiazole-$CH_2N^+H_3$)-1H at 4.21 ppm and 1H at 3.89 ppm (D, J=13 Hz, $CH_2SCO$)-3H at 3.79 ppm (S, $CH_3ON$)-1H at 3.67 ppm and 1H at 3.39 ppm (D, J=17 Hz, $CH_2S$)-.

NMR n° 70

1H at 9.52 ppm (D, J=9 Hz, NHCO)-1H at 8.90 ppm (T, J=7 Hz, Ar $CH_2$ NH CO)-3H at 8.00 ppm (S.e., $N^+H_3$)-2H at 7.80 ppm (M, H aromatics ortho COS)-2H at 7.53 ppm (M, H aromatics meta and para COS)-2H at 7.30 ppm (S.e., $NH_2$ thiazole)-1H at 6.68 ppm (S, H thiazole)-1H at 5.69 ppm (D de D, $J_1$=9 Hz $J_2$=4 Hz, $H_7$)-1H at 5.08 ppm (D, J=4 Hz, $H_6$)-1H at 4.39 ppm (D, J=7 Hz, Ar $CH_2$ NH)-1H at 4.27 ppm and 1H at 3.95 ppm (D, J=13 Hz, $CH_2SCO$)-3H at 3.79 ppm (S, $CH_3ON$)-1H at 3.66 ppm (D, J=17 Hz, $CH_2S$)-2H at 3.55 ppm (M, $NHCOCH_2N$)-1H at 3.34 ppm (D, J=17 Hz, $CH_2S$)-.

NMR n° 71

1H at 9.55 ppm (D, J=9 Hz, NHCO)-1H at 8.89 ppm (T, J=7 Hz, Ar $CH_2$ NHCO)-3H at 8.02 ppm (S.e., $N^+H_3$)-2H at 7.83 ppm (D, J=8 Hz, H aromatics ortho COS)-2H at 7.40 ppm (D, J=8 Hz, H aromatics meta COS)-2H 7.28 ppm (S.e., $NH_2$ thiazole)-1H 6.68 ppm (S, H thiazole)-1H at 5.71 ppm (D of D, $J_1$=9 Hz $J_2$=4 Hz, $H_7$)-1H at 5.11 ppm (D, J=4 Hz, $H_6$)-2H at 4.39 ppm (D, J=7 Hz, Ar $CH_2$ NH)-1H at 4.27 ppm and 1H at 3.95 ppm (D, J=13 Hz, $CH_2SCO$)-3H at 3.79 ppm (S, $CH_3ON$)-1H at 3.78 ppm (D, J=17 Hz, $CH_2S$)-2H at 3.63 ppm (M, $COCO_2N^+$)-1H at 3.34 ppm (D, J=17 Hz, $CH_{2S}$)-.

NMR n° 72

1H at 9.40 ppm (D, J=9 Hz, CO NH)-5H at 7.80 ppm (M, $CH_2N^+H_3$ and H aromatic ortho COS)-1H at 7.56 ppm (D, J=8 Hz, H aromatic para COS)-1H at 7.50 ppm (T, J=8 Hz, H aromatic meta COS)-2H at 7.23 ppm (S.e., $NH_2$ thiazole)-1H at 6.68 ppm (S, H thiazole)-1H at 5.75 ppm (D of D, $J_1$=9 Hz $J_2$=4 Hz, $H_7$)-1H at 5.10 ppm (D, J=4 Hz, $H_6$)-1H at 4.28 ppm and 1H at 3.94 ppm (D, J=13 Hz, $CH_2SCO$)-1H at 3.69 ppm and 1H at 3.36 ppm (D, J=17 Hz, $CH_2S$)-3H at 3.00 ppm (M, Ar—CH—$CH_2\overset{+}{N}$)— 6H at 1.40 ppm (2S, $(CH_3)_2C$)-2H at 1.22 ppm (D, J=7 Hz, Ar—CH—$CH_3$) —

NMR n° 73

1H at 12.70 ppm (S, thiazole NHCO)-1H at 9.45 ppm (D, J=9 Hz, NHCO)-1H at 8.05 ppm (S, H thiazole ester)-3H at 7.80 ppm (S.e., $N^+H_3$)-2H at 7.36 ppm (S.e., $NH_2$ thiazole)-1H at 6.69 ppm (S, H thiazole amine)-1H at 5.70 ppm (D of D, $J_1$=9 Hz $J_2$=4 Hz, $H_7$)-1H at 5.07 ppm (D, J=4 Hz, $H_6$)-1H at 4.24 ppm and 1H at 3.80 ppm (D, J=13 Hz, $CH_2SCO$)-1H at 3.66 ppm and 1H at 3.40 ppm (D, J=17 Hz, $CH_2S$)-2H at 3.05 ppm (M, $CH_2N^+H_3$)-2H at 2.80 ppm (M, $CH_2CH_2N^+H_3$)-6H at 1.40 ppm (2S, $(CH_3)_2C$)-.

NMR n° 74

1H at 12.60 ppm (S, thiazole NHCO)-1H at 9.55 ppm (D, J=9 Hz, NHCO-1H at 8.05 ppm (s, H thiazole ester)-3H at 7.83 ppm (S.e., $NH_3^+$)-2H at 7.32 ppm (S.e., $NH_2$ thiazole)-1H at 6.71 ppm (S, H thiazole amine)-1H at 5.70 ppm (D of D, $J_1$=9 Hz $J_2$=4 Hz, $H_7$)-1H at 5.07 ppm (D, J=4 Hz, $H_6$)-1H at 4.25 ppm and 1H at 3.84 ppm (D, J=13 Hz, $CH_2SCO$)-3H at 3.82 ppm (S, $CH_3ON$)-1H at 3.65 ppm and 1H at 3.31 ppm (D, J=17 Hz, $CH_2S$)-2H at 3.06 ppm (M, $CH_2N^+H_3$)-2H at 2.80 ppm (M, CO—$CH_2CH_2{}^+N$)-.

NMR n° 75

1H at 9.53 ppm (D, J=9 Hz, NHCO)-5H at 7.85 ppm (M, $N^+H_3$ and H aromatic ortho COS)-1H at 7.55 ppm (D, J=8 Hz, H aromatic para COS)-1H at 7.00 ppm (T, J=8 Hz, H aromatic meta COS)-2H at 7.30 ppm (S.e., $NH_2$ thiazole)-1H at 6.70 ppm (S, H thiazole)-1H at 5.70 ppm (D of D, $J_1$=9 Hz, $J_2$=4 Hz, $H_7$)-1H at 5.05 ppm (D, J=4 Hz, $H_6$)-1H at 4.25 ppm and 1H at 3.93 ppm (D, J=13 Hz, $CH_2$ SCO)-3H at 3.80 ppm (S, $CH_3ON$)-1H at 3.67 ppm and 1H at 3.32 ppm (D, J=17 Hz, $CH_2S$)-3H at 3.01 ppm (M,

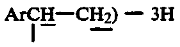

at 1.21 ppm (D, J=7 Hz,

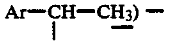

NMR n° 76

1H at 10.55 ppm (S, Ar NHCO)-1H at 9.53 ppm (D, J=9 Hz, CONH)-2H at 7.84 ppm (D, J=8 Hz, H aromatics ortho COS)-3H at 7.80 ppm (S.e., $CH_2N^+H_3$)-2H at 7.71 ppm (D, J=8 Hz, H aromatics meta COS)-2H at 7.30 ppm (S.e., $NH_2$ thiazole)-1H at 6.71 ppm (S, H thiazole)-1H at 5.72 ppm (D of D, $J_1$=9 Hz $J_2$=4 Hz, $H_7$)-1H at 5.08 ppm (D, J=4 Hz, $H_6$)-1H at 4.26 ppm and 1H at 3.92 ppm (D, J=13 Hz, $CH_2SCO$)-3H at 3.79 ppm (S, $CH_3ON$)-1H at 3.70 ppm and 1H at 3.34 ppm (D, J=17 Hz, $CH_2S$)-2H at 3.05 ppm (M, $CH_2N^+H_3$)-2h at 2.70 ppm (M, $CH_2CH_2N^+h_3$.

NMR n° 77

1H at 10.95 ppm (ArNHCO)-1H at 9.55 ppm (D, J=9 Hz, CONH)-2H at 8.90 ppm (S.e., $NH_2$—$CH_3$)-2H at 7.95 ppm (D, J=8 Hz, H aromatics ortho SCO)-2H at 7.75 ppm (D, J=8 Hz, H aromatics meta SCO)-2H at 7.30 ppm (S.e., $NH_2$ thiazole 1H at 6.70 ppm (S, H thiazole)-1H at 5.70 ppm (D of D, $J_1$=9 Hz, $J_2$=4 Hz, $H_7$)-1H at 5.08 ppm (D, J=4 Hz, $H_6$)-1H at 4.30 ppm (D, J=13 Hz, $CH_2SCO$)-3H at 3.90 ppm (M, $CH_2N^+$ and $CH_2SCO$)-3H at 3.80 ppm (S, $NOCH_3$)-1H at 2.65 ppm (D, J=17 Hz, $CH_2S$)-1H at 3.40 ppm (D, J=17 Hz, $CH_2S$)-3H at 2.60 ppm (S.e., —$N^+H_2$—$CH_3$)-.

NMRn° 78

1H at 10.12 ppm (S, ArNHCO)-1H at 9.39 ppm (D, J=9 Hz, NHCO)-1H at 7.90 ppm (D, J=8 Hz, H aromatics ortho SCO)-3H at 7.80 ppm S.e., $CH_2N^+H_3$)-2H at 7.75 ppm (D, J=8 Hz, H aromatics meta SCO)-2H at 7.50 ppm (S.e., $NH_2$ thiazole)-1H at 6.71 ppm (S, H thiazole)-1H at 5.76 ppm (D of D, $J_1$=9 Hz, $J_2$=4 Hz, $H_7$)-1H at 5.11 ppm (D, J=4 Hz, $H_6$)-1H at 4.22 ppm (D, J=13 Hz, $CH_2SCO$)-1H at 3.93 ppm (D, J=13 Hz, $CH_2SCO$)-1H at 3.71 ppm (D, J=17 Hz, $CH_2S$)-1H at 3.45 ppm (D, J=17 Hz, $CH_2S$)-2H at 3.07 ppm (M, $CH_2N^+H_3$)-2H at 2.73 ppm (M, $CH_2CH_2N^+H_3$)-6H at 1.14 ppm (S,

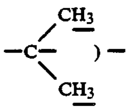

NMRn° 79

1H at 9.45 ppm (D, J=9 Hz, CONH)-1H at 8.58 ppm (S, H thiazole ester)-3H at 8.53 ppm (S.e., $CH_2N^+H_3$)-2H at 7.50 ppm (S.e. $NH_2$ thiazole)-1H at 6.70 ppm (S, H thiazole)-1H at 5.80 ppm (D of D, $J_1$=9 Hz, $J_2$=4 Hz, $H_7$)-1H at 5.20 ppm (D, J=4 Hz, $H_6$)-2H at 4.50 ppm (S.e., $CH_2N^+H_3$)-1H at 4.20 ppm (D, J=13 Hz, $CH_2SCO$)-1H at 3.90 ppm (D, J=13 Hz, $CH_2SCO$)-1H at 3.71 ppm (D, J=17 Hz, $CH_2S$)-1H at 3.38 ppm (D, J=17 Hz, $CH_2S$)-6H at 1.42 ppm (S,

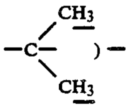

NMRn° 80

1H at 9.70 ppm (D, J=9 Hz, CONH)-3H at 8.15 ppm (S.e., $CH_2N^+H_3$)-2H at 7.45 ppm (S.e., $NH_2$ thiazole)-2H at 7.40 ppm (D, J=8 Hz, H aromatics meta O)-2H at 7.05 ppm (D, J=8 Hz, H aromatics ortho O)-1H at 6.76 ppm (S, H thiazole)-1H at 5.77 ppm (D of D, $J_1$=9 Hz, $J_2$=4 Hz, $H_7$)-1H at 5.12 ppm (D, J=4 Hz, $H_6$)-2H at 5.00 ppm (S, $CH_2O$-Ar)-1H at 4.20 ppm (D, J=13 Hz, $CH_2SCO$)-2H at 4.00 ppm (M, $CH_2N^+H_3$)-3H at 3.85 ppm (S, $NOCH_3$)-1H at 3.76 ppm (D, J=13 Hz, $CH_2SCO$)-1H at 3.70 ppm (D, J=17 Hz, $CH_2S$)-1H at 3.30 ppm (D, J=17 Hz, $CH_2S$).

NMRn° 81

1H at 9.42 ppm (D, J=9 Hz, CONH)-3H at 8.07 ppm (S.e., $CH_2N^+H_3$)-2H at 7.41 ppm (D, J=8 Hz, H aromatics meta O)-2H at 7.40 ppm (S.e., $NH_2$ thiazole)-2H at 7.00 ppm (D, J=8 Hz, H aromatics ortho O)-1H at 6.66 ppm (S, H thiazole)-1H at 5.80 ppm (D of D, $J_1$=9 Hz, $J_2$=4 Hz, $H_7$)-1H at 5.09 ppm (D, J=4 Hz, $H_6$)-2H at 4.96 ppm (S, $CH_2OAr$)-1H at 4.10 ppm (D, J=13 Hz, $CH_2SCO$)-2H at 3.80 ppm (M, $ArCH_2N^+H_3$)-1H at 3.75 ppm (D, J=13 Hz, $CH_2SCO$)-1H at 3.60 ppm (D, J=17 Hz, $CH_2S$)-1H at 3.30 ppm (D, J=17 Hz, $CH_2S$)-6H at 1.41 ppm (2S,

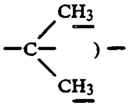

NMRn° 82

1H at 10.56 ppm (S, ArNHCO)-1H at 9.55 ppm (D, J=9 Hz, CONH)-2H at 7.90 ppm (D, J=8 Hz, H aromatics ortho SCO)-3H at 7.75 ppm (S.e., $CH_2N^+H_3$)-2H at 7.70 ppm (D, J=8 Hz, H aromatics meta SCO)-2H at 7.45 ppm (S.e., $NH_2$ thiazole)-1H at 6.66 ppm (S, H thiazole)-1H at 5.74 ppm (D of D, $J_1$=9 Hz, $J_2$=4 Hz, $H_7$)-1H at 5.11 ppm (D, J=4 Hz, $H_6$)-1H at 4.25 ppm (D, J=13 Hz, $CH_2SCO$)-1H at 3.92 ppm (D, J=13 Hz, $CH_2SCO$)-2H at 3.84 ppm (D, J=7 Hz, N—$OCH_2$—)-1H at 3.66 ppm (D, J=17 Hz, $CH_2S$)-1H at 3.34 ppm (D, J=17 Hz, $CH_2S$)-2H at 3.05 ppm (M, $CH_2N^+H_3$)-2H at 2.68 ppm (T, J=7 Hz, $CH_2CH_2N^+H_3$)-1H at 3.05 ppm (M, N—$OCH_2$<CH)-2H at 0.46 ppm and 2H at 0.23 ppm (2M, $CH_2$ cyclopropane).

EXAMPLE 85

7-[2-(2-amino 4-thiazolyl) 2-(2-carboxy 2-propyl oxyimino) acetamido] 3-[(4-piperidyl) carbonylthiomethyl] 3-cepheme 4-carboxylic acid bis trifluoracetate syn isomer (SR 42318)

(I) $R_1=R_2=H$ $R_3=COOH$ X=S n=O

B = 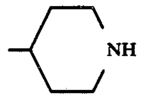

(a) 1-tertiobutoxycarbonyl 4-piperidyl thiocarboxylic acid.

This is prepared from 9.16 g of 1-tertiobutoxycarbonyl 4-piperidyl carboxylic acid, according to the method used in example 64a. The crude oily product is used as is.

(b) 7-amino 3-[1-tertiobutoxycarbonyl 4-piperidyl) carbonylthiomethyl] 3-cepheme carboxylic acid.

9 g of 7-aminocephalosporanic acid and 2.8 g of sodium bicarbonate are dissolved in 100 ml of phosphate buffer pH 6.65. The solution is heated to 50° C. under nitrogen atmosphere, then the solution composed of the thioacid obtained above and 3.36 g of sodium bicarbonate in 70 ml of phosphate buffer pH 6.65 is added.

A precipitate forms during the reaction and the pH tends to go up. It is kept to 6.35 by adding a 10% solution of phosphoric acid. After 4 hours, the reaction medium is cooled down to 0° C. and the crystals are drained. Then they are washed in cold water, acetone, ether and finally in hexane.

Weight: 7.5 g

IR Spectrum: γCO βlactam 1810 $cm^{-1}$.

(c) 7-[2-(2-tritylamino 4-thiazolyl) 2-(2-tertiobutoxycarbonyl 2-propyl oxyimino) acetamido] 3-[(1-tertiobutoxycarbonyl 4-piperidyl) carbonylthiomethyl] 3-cepheme 4-carboxylic acid syn isomer.

11.4 g of the acid obtained above are placed in suspension in 250 ml of anhydrous dichloromethane and the mixture is cooled down to +5° C. A solution of 3.47 ml of triethylamine and 9.5 ml of dimethylaniline in 20 ml of dichloromethane is then added dropwise followed by a solution of 7.94 ml of chlorotrimethylsilane in 10 ml of dichloromethane, also added dropwise. The temperature is allowed to return to around 20° C. and the mixture is left at that temperature for two hours.

The temperature is then brought down again to +5° C., and 14 g of chloride of 2-(2-tritylamino 4-thiazolyl) 2-(2-tertiobutoxycarbonyl 2-propyl oxyimino) acetic acid syn isomer are added in small quantities. The reaction mixture is stirred for 1 hour at ambient temperature, and placed in a refrigerator for 15 hours.

40 ml of water are then added and the dichloromethane is evaporated. The residual is taken up in 600 ml of ethyl acetate and 300 l ml of buffer sulfate pH 2. The organic phase is decanted and washed again with 150 ml of buffer sulfate pH 2, and then with 100 ml of water.

After drying over magnesium sulfate, the organic solution is concentrated to about 150 ml. It is then poured dropwise in 1200 ml of hexane under strong stirring. After 30 minutes of that stirring, the solid product is drained, washed in hexane and dried in vacuo.

20.8 g of the expected product are then obtained.

NMR Spectrum 1H at 9.32 ppm (D, J=9 Hz, CO NH)-1H at 8.80 ppm (S, NH-tritye)-15H at 7.25 ppm (M, H aromatics-trityle)-1H at 6.60 ppm (S, H thiazole)-1H at 5.66 ppm (D of D, $J_1=9$ Hz $J_2=4$ Hz, $H_7$)-1H at 5.06 ppm (D, J=4 Hz, $H_6$)-1H at 4.00 ppm at 1H at 3.75 ppm (D, J13 Hz, $CH_2SCO$)-1H at 3.56 ppm at 1H at 3.32 ppm (D, J=17 Hz, $CH_2S$)-2H at 3.85 ppm, 3H at 2.75 ppm, 2H at 1.75 ppm and 2H at 1.38 ppm (M, CH and $CH_2$ piperidine)-2H at 1.34 ppm (2S, COOtBu, N-Boc, —$C(CH_3)_2$).

(d) SR 42318

The compound obtained above is deprotected by the trifluoracetic acid as indicated in Example 1c. The expected product is obtained in the same way.

NMR Spectrum 1H at 9.40 ppm (D, J=9 Hz, NHCO)-1H at 8.60 ppm at 8.35 ppm (2 S.E., $NH_2^+$ piperidine)-2H at 7.30 ppm (S.e, $NH_2$thiazole)-1H at 6.66 ppm (S, H thiazole)-1H at 5.75 ppm (D of D, $J_1=9$ Hz $J_2=4$ Hz, $H_7$)-1H at 5.08 ppm (D, J=4 Hz, $H_6$)-1H at 4.05 ppm 1H at 3.75 ppm (D, J=13 Hz, $CH_2SCO$)-1H at 3.61 ppm (D, J=17 Hz, $CH_2S$)-3H at 3.25 ppm (M, $CH_2S$ and H piperidine $\alpha NH_2^+$ equatorial)-3H at 2.90 ppm (M, SCO—<CH and H piperidine $\alpha NH_2^+$ axial)-2H at 1.95 ppm (M, H piperidine $\beta NH_2^+$ equatorial)-2H 1.70 ppm (M, H piperidine $\beta NH_2^+$ axials)-6H at 1.42 ppm (2S, $(CH_3)_2C$).

EXAMPLES 86 to 100

(a) By operating as in Example 85b, but by varying the thioacid, one obtains the 7-amino 3-cepheme 4-carboxylic acids variously substituted in 3, and listed in Table III.

TABLE III

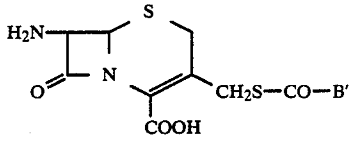

| B' | IR Spectrum γCO lactam | ELEMENTARY ANALYSIS Calculated | Found |
|---|---|---|---|
| 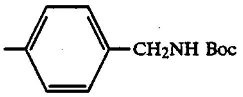 | 1810 $cm^{-1}$ | C: 52,59<br>H: 5,25<br>N: 8,76 | 52,27<br>5,22<br>8,40 |
| 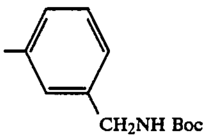 | 1810 $cm^{-1}$ | C: 52,59<br>H: 5,25<br>N: 8,76 | 52,14<br>5,13<br>8,72 |
| 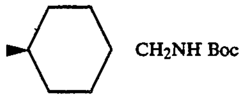 | 1805 $cm^{-1}$ | C: 51,94<br>H: 6,43<br>N: 8,65 | 51,75<br>6,39<br>8,38 |
| 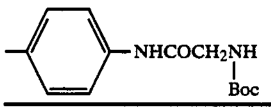 | 1815 $cm^{-1}$ | C: 50,56<br>H: 5,01<br>N: 10,72 | 50,32<br>5,13<br>10,59 |

(b) The different products (I)(X=S) listed in Table IV hereafter are obtained with the products prepared according to the method of Example 85c and d, using different acid chlorides.
TABLE IV
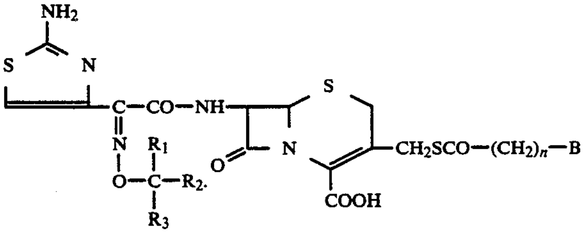
| SR No. | n | $R_1$ | $R_2$ | $R_3$ | B | IR Spectrum Compound 7 $\gamma CO$ $cm^{-1}$ | NMR No. |
|---|---|---|---|---|---|---|---|
| 42316 | O | H | H | H | 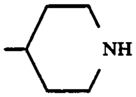 | 1790–1730 1690 | 83 |
| 42317 | O | H | H | H | 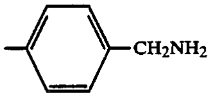 | 1790–1720 | 84 |
| 42319 | O | $CH_3$ | $CH_3$ | COOH | 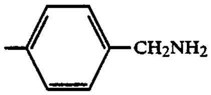 | 1795–1720 | 85 |
| 42802 | O | $CH_3$ | $CH_3$ | COOH | 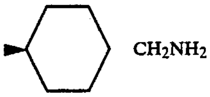 | 1790–1720 1690 | 86 |
| 42889 | O | H | H | H | 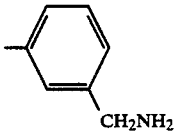 | 1790–1710 | 87 |
| 42882 | O | $CH_3$ | $CH_3$ | COOH | 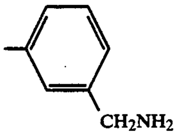 | 1790–1715 | 88 |
| 43017 | O | $(CH_2)_3$ | | COOH | 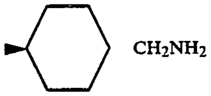 | 1790–1715 1690 | 89 |
| 43019 | O | H | $CH_3$ | COOH | 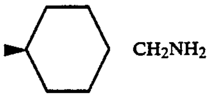 | 1790–1720 1690 | 90 |
| 43020 | O | H | H | COOH | 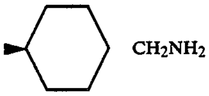 | 1790–1715 1690 | 91 |

TABLE IV-continued

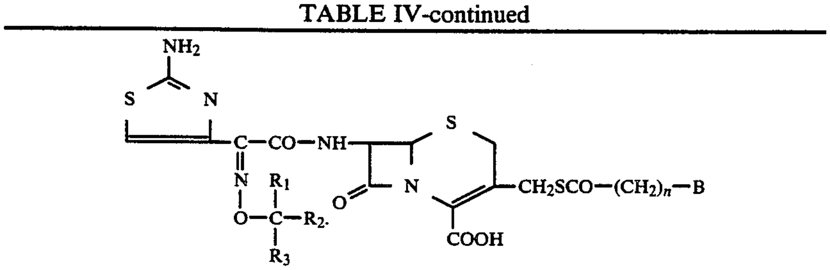

| SR No. | n | $R_1$ | $R_2$ | $R_3$ | B | IR Spectrum Compound 7 γCO $cm^{-1}$ | NMR No. |
|---|---|---|---|---|---|---|---|
| 43021 | O | H | H | 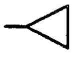 | 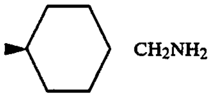 | 1790-1685 | 92 |
| 43023 | O | H | H | H | 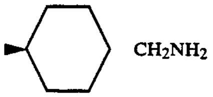 | 1790-1690 | 93 |
| 43520 | O | H | H | H | 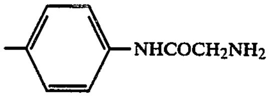 | 1785-1690 (Methylyne chloride) | 94 |
| 43522 | O | H | H | 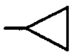 | 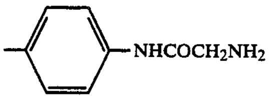 | 1785-1690 (Methylene chloride) | 95 |
| 43524 | O | $CH_3$ | $CH_3$ | COOH | 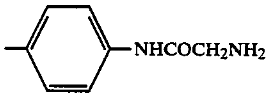 | 1785-1715 (Methylene chloride) | 96 |
| 43697 | O | H | H | COOH | 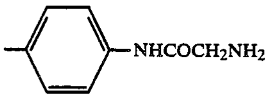 | 1785-1715 | 97 |

NMR n° 83

1H at 9.50 ppm (D, J=9 Hz, CO NH)-1H at 8.70 ppm and 1H at 8.45 ppm (2 S.e., $NH_2^+$ piperidine)-2H at 7.30 ppm (S.e., $NH_2$ thiazole)-1H at 6.71 ppm (S, H thiazole)-1H at 5.76 ppm (D of D, $J_1$=9 Hz $J_2$=4 Hz, $H_7$)-1H at 5.07 ppm (D, J=4 Hz, $H_6$)-1H at 4.05 ppm (D, J=13 Hz, $CH_2SCO$)-4H at 3.78 ppm (M, $CH_3ON$ and $CH_2SCO$)-1H at 3.58 ppm (D, J=17 Hz, $CH_2S$)-3H at 3.27 ppm (M, $CH_2S$ and H equatorials piperidine αNH-$2^+$)-3H at 2.95 ppm (M, SCO—<CH and H axials piperidine $\alpha NH_2$)-2H at 2.00 ppm and 2H and 1.70 ppm (M, H piperidine $\beta NH_2^+$).

NMR n° 84

1H at 9.50 ppm (D, J=9 Hz, CO NH)-3H at 8.40 ppm (S.e., $CH_2NH_3^+$)-2H at 7.95 ppm (D, J=7 Hz, H aromatics ortho CO)-2H at 7.55 ppm (D, J=7 Hz, H aromatics meta CO)-2H at 7.30 ppm (S.e., $NH_2$ thiazole)-1H at 6.73 ppm (S, H thiazole)-1H at 5.71 ppm (D of D, $J_1$=9 Hz $J_2$=4 Hz, $H_7$)-1H at 5.08 ppm (D, J=4 Hz, $H_6$)-1H at 4.26 ppm (D, J13 Hz, $CH_2SCO$)-2H at 4.12 ppm (M, $CH_2N^+H_3$)-1H at 3.92 ppm (D, J=13 Hz, $CH_2SCO$)-3H at 3.78 ppm (S, $NOCH_3$)-1H at 3.68 ppm (D, J=17 Hz, $CH_2S$)-1H at 3.40 ppm (D, J=17 Hz, $CH_2S$).

NMR n° 85

1H at 9.45 ppm (D, J=9 Hz, NHCO)-3H at 8.25 ppm (S.e., $CH_2NH_3^+$)-2H at 7.95 ppm (D, J=7 Hz, H aromatics ortho CO)-2H at 7.55 ppm (D, J=7 Hz, H aromatics meta CO)-2H at 7.20 ppm (S.e., $NH_2$ thiazole)-1H at 6.68 ppm (S, H thiazole)-1H at 5.79 ppm (D of D, $J_1$=9 Hz $J_2$=4 Hz, $H_7$)-1H at 5.10 ppm (D, J=4 Hz, $H_6$)-1H at 4.27 ppm (D, J=13 Hz, $CH_2SCO$)-2H at 4.10 ppm (M, $CH_2N^+H_3$)-1H at 3.95 ppm (D, J=13 Hz, $CH_2SCO$)-1H at 3.69 ppm (D, J=17 Hz, $CH_2S$)-1H at 3.40 ppm (D, J=17 Hz, $CH_2S$)-6H at 1.40 ppm (2S, $(CH_3)_2C$).

NMR n° 86

1H at 9.45 ppm (D, J=9 Hz, NHCO)-3H at 7.75 ppm (S.e., $CH_2NH_3^+$2H at 7.45 ppm (S.e., $NH_2$ thiazole)-1H at 6.70 ppm (S, H thiazole)-1H at 5.80 ppm (D of D, $J_1$=9 Hz $J_2$=4 Hz, $H_7$)-1H at 5.20 ppm (D, J=4 Hz, $H_6$)-1H at 4.00 ppm and 1H at 3.74 ppm (D, J=13 Hz, $CH_2SCO$)-1H at 3.60 ppm (D, J=17 Hz, $CH_2S$)-1H at 3.25 ppm (D, J=17 Hz, $CH_2S$)-2H at 2.60 ppm (M, $CH_2N^+$)-1H at 2.45 ppm (M, SCO<CH)-4H at 1.85 ppm, 3H at 1.40 ppm and 2H at 1.00 ppm (M, H cyclohexane)-6H at 1.40 ppm (2S, $(CH_3)_2C$).

NMR n° 87

1H at 9.55 ppm (D, J=9 Hz, NHCO)-3H at 8.35 ppm (S.e., $CH_2NH_3^+$)-1H at 8.05 ppm (S, H aromatic ortho COS and ortho $CH_2NH_3^+$)-1H at 7.90 ppm (D, J=8 Hz, H aromatic ortho COS and para $CH_2N^+H_3$)-1H at 7.72 ppm (D, J=8 Hz, H aromatic para COS)-1H at 7.55 ppm (T, J=8 Hz, H aromatic meta COS)-1H at 6.72 ppm (S, H thiazole)-1H at 5.74 ppm (D of D, $J_1$=9 Hz, $J_2$=4 Hz, $H_7$)-1H at 5.08 ppm (D, J=4 Hz, $H_6$)-1H at 4.30 ppm (D, J=13 Hz, $CH_2SCO$)-2H at 4.10 ppm (M, Ar $CH_2N^+$)-1H at 3.95 ppm (D, J=13 Hz, $CH_2SCO$)-3H at 3.80 ppm (S, $CH_3ON$)-1H at 3.70 ppm and 1H at 3.40 ppm (D, J=17 Hz, $CH_2S$).

NMR n° 88

1H at 9.42 ppm (D, J=9 Hz, CO NH)-3H at 8.25 ppm (S.e., $CH_2N^+H_3$)-1H at 8.00 ppm (S, H aromatic ortho COS et ortho $CH_2N^+$)-1H at 7.88 ppm (D, J=8 Hz, H aromatic ortho COS and para $CH_2N^+$)-1H at 7.75 ppm (D, J=8 Hz, H aromatic para COS)-1H at 7.55 ppm (T, J=8 Hz, H aromatic meta COS)-2H at 7.40 ppm (S.e., $NH_2$ thiazole)-1H at 6.67 ppm (S, H thiazole)-1H at 5.81 ppm (D of D, $J_1$=9 Hz $J_2$=4 Hz, $H_7$)-1H at 5.12 ppm (D, J=4 Hz, $H_6$)-1H at 4.30 ppm (D, J=13 Hz, $CH_2SCO$)-2H at 4.08 ppm (M, Ar $CH_2N^+$)1H at 3.95 ppm (D, J=13 Hz, $CH_2SCO$)-1H at 3.71 ppm et 1H at 3.40 ppm (D, J=17 Hz, $CH_2S$)-6H at 1.43 ppm (2S, $(CH_3)_2C$).

NMR n° 89

1H at 9.50 ppm (D, J=9 Hz, CO NH)-3H at 7.75 ppm (S.e., $CH_2NH_3^+$)-2H at 7.30 ppm (S.e., $NH_2$ thiazole)-1H at 6.70 ppm (S, e,uns/H/ thiazole)-1H at 5.81 ppm (D of D, $J_1$=9 Hz $J_2$=4 Hz, $H_7$)-1H at 5.14 ppm (D, J=4Hz, $H_6$)-1H at 4.02 ppm and 1H at 3.74 ppm (D, J=13 Hz, $CH_2SCO$)-1H at 3.63 ppm and 1Hz at 3.27 ppm (D, J=17 Hz, $CH_2S$)-2H at 2.58 ppm (M, $CH_2N^+$)-1H at 2.50 ppm (M, SCO—<CH)-4H at 2.30 ppm (M

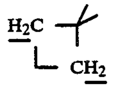

6H at 1.85 ppm, 1H at 1.45 ppm, 2H at 1.25 ppm and 2H at 0.95 ppm (M,

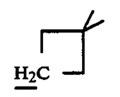

and CH and $CH_2$ cyclohexane)-.

NMR n° 90

1H at 9.45 ppm (2D, J=9 Hz, CONH)° -3H at 7.75 ppm (S.e., $CH_2N^+H_3$)-2H at 7.25 ppm (S, e., $NH_2$ thiazole)-1H at 6.70 ppm (S, H thiazole)-1H at 5.80 ppm (2Q, $J_1$=9 Hz $J_2$=4 Hz, $H_7$)° -1H at 5.10 ppm (D, J=4 Hz, $H_6$)-1H at 4.56 ppm (Q, J=7 Hz,

NOCH—$CH_3$) — 1H at 4.00 ppm and 1H at 3.74 ppm (D, J=13 Hz, $CH_2SCO$)-1H at 3.60 ppm and 1H at 3.22 ppm (D, J=7 Hz, $CH_2S$)-2H at 2.60 ppm (M, $CH_2N^+H_3$)-1H at 2.50 ppm (M, SCO—<CH)-4H at 1.80 ppm, 1H at 1.44 ppm, 2H at 1.30 ppm and 2H at 1.00 ppm (M, H cyclohexane)-3H at 1.36 ppm (D, J=7 Hz,

N—O—CH—$CH_3$) —

° Signals split because of the oxime diastereoisomery.

NMR n° 91

1H at 9.50 ppm (D, J=9 Hz, CO NH)-3H at 7.82 ppm (S, e., $CH_2N^+H_3$)-2H at 7.30 ppm (S.e., $NH_2$ thiazole)-1H at 6.76 ppm (S, H thiazole)-1H at 5 74 ppm (D of D, $J_1$=9 Hz $J_2$=4 Hz, $H_7$)-1H at 5.08 ppm (D, J=4 Hz, $H_6$)-2H at 4.52 ppm (S, N O $CH_2$-COOH)-1H at 4 00 ppm and 1H at 3.71 ppm (D, J=13 Hz, $CH_2SCO$)-1H at 3.56 ppm and 1H at 3.21 ppm (D, J=17 Hz, $CH_2S$)-2H at 2.58 ppm (M, $CH_2$ $NH_3^+$)-1H at 2.51 ppm (M, SCO<CH)-4H at 1.90 ppm, 1H at 1.45 ppm, 2H at 1.30 ppm et 2H at 0.95 ppm (M, H cyclohexane)-

NMR n° 92

1H at 9.55 ppm (D, J=9 Hz, CONH)-3H at 7.80 ppm (S.e., $CH_2NH_3^+$)-2H at 7.23 ppm (S.e., $NH_2$ thiazole)-1H at 6.68 ppm (S, H thiazole)-1H at 5.73 ppm (D of D, $J_1$=9 Hz $J_2$=4 Hz, $H_7$)-1H at 5.06 ppm (D, J=4 Hz, $H_6$)-1H at 4.00 ppm and 1H at 3.70 ppm (D, J=13 Hz, $CH_2SCO$)-2H at 3.90 ppm (D, J=7 Hz, N-O-$CH_2$-)-1H at 3.60 ppm and 1H at 3.23 ppm (D, J=17 Hz, $CH_2S$)-2H at 2.58 ppm (M, $CH_2N^+H_3$)-1H at 2.51 ppm (M, SCO—<CH)-4H at 1.85 ppm, 1H at 1.44 ppm, 2H at 1.30 ppm and 2H at 0.95 ppm (M, H cyclohexane)-1H at 1.08 ppm, 2H at 0.45 ppm and 2H at 0.23 ppm (H cyclopropane)-.

NMR n° 93

1H at 9.55 ppm (D, J=9 Hz, CONH)-3H at 7.80 ppm (S.e., $CH_2NH_3^+$)-2H at 7.20 ppm (S.e., $NH_2$ thiazole)-1H at 6.69 ppm (S, H thiazole)-1H at 5.68 ppm (D of D, $J_1$=9 Hz, $J_2$=H Hz, $H_7$)-1H at 5.05 ppm (D, J=4 Hz, $H_6$)-1H at 4.00 ppm and 1H at 3.70 ppm (D, J=13 Hz, $CH_2SCO$)-3H at 3.75 ppm (S, $CH_3ON$)-1H at 3.60 ppm and 1H at 3.25 ppm (D, J=17 Hz, $CH_2S$)-2H at 2.57 ppm (M, $CH_2NH_3^+$)-1H at 2.50 ppm (M, SCO—<CH)-4H at 1.90 ppm, 1H at 1.47 ppm, 2H at 1.30 ppm and 2H at 0.97 ppm (M, H cyclohexane)-.

NMR n° 94

1H at 10.80 ppm (S, ArNHCO)-1H at 9.55 ppm (D, J=9 Hz, NHCO)-3H at 8.16 ppm (S.e., $CH_2N^+H_3$)-2H at 7.92 ppm (D, J=8 Hz, H aromatics ortho SCO)-2H at 7.75 ppm (D, J=8 Hz, aromatics meta SCO)-2H at 7.35 ppm (S.e., $NH_2$ thiazole)-1H at 6.67 ppm (S, H thiazole)-1H at 5.80 ppm (D of D, $J_1$=9 Hz, $J_2$=4 Hz, $H_7$)-1H at 5.08 ppm (D, J=4 Hz, $H_6$)-1H at 4.26 ppm (D, J=13 Hz, $CH_2SCO$)-1H at 3.91 ppm (D. J=13 Hz, $CH_2SCO$)-3H at 3.80 ppm (S, $CH_3ON$)-1H at 3.67 ppm (D, J=17 H, $CH_2S$)-1H at 3.32 ppm (D, J=17 Hz, $CH_2S$)-.

NMR n° 95

1H at 10.84 ppm (S, ArNHCO)-1H at 9.57 ppm (D, J=9 Hz, NHCO)-3H at 8.15 ppm (S.e., $CH_2N^+H_3$)-2H at 7.95 ppm (D, J=8 Hz, H aromatics ortho SCO)-2H at 7.74 ppm (D, J=8 Hz, H aromatics metal SCO)-2H at 7.55 ppm (S.e., $NH_2$ thiazole)-1H at 6.66 ppm (S, H thiazole)-1H at 5.80 ppm (D of D, $J_1$=9 Hz, $J_2$=4 Hz, $H_7$)-1H at 5.10 ppm (D, J=4 Hz, $H_6$)-1H at 4.25 ppm (D, J=13 Hz, $CH_2SCO$)-1H at 3.95 ppm (D, J=13 Hz, $CH_2SCO$)-2H at 3.84 ppm (D, J=7 Hz, N—O—$CH_2$—)-2H at 3.82 ppm (M, $CH_2N^+H_3$)-1H at 3.66 ppm (D, J=17 Hz, $CH_2S$)-1H at 3.34 ppm (D, J=17 Hz, $CH_2S$)-1H at 1.10 ppm (M, N—O—$CH_2$—<CH)-2H at 0.55 ppm and 2H at 0.23 ppm ($CH_2$ cyclopropane)-.

NMR n° 96

1H at 10.85 ppm (S, ArNHCO)-1H at 9.45 ppm (D, J=9 Hz, CONH)-3H at 8.15 ppm (S.e., $CH_2N^+H_3$)-2H at 7.92 ppm (D, J=8 Hz, H aromatics ortho SCO)-2H at 7.75 ppm (D, J=8 Hz, H aromatics meta SCO)-2H at 7.50 ppm (S.e., $NH_2$ thiazole)-1H at 6.68 ppm (S, H thiazole)-1H at 5.79 ppm (D of D, $J_1$=9 Hz, $J_2$=4 Hz, $H_7$)-1H at 5.12 ppm (D, J=4 Hz, $H_6$)-1H at 4.30 ppm (D, J=13 Hz, $CH_2SCO$)-1H at 3.92 ppm (D, J=13 Hz, $CH_2SCO$)-2H at 3.79 ppm (M, $CH_2N^+H_3$)-1H at 3.67 ppm (D, J=17 Hz, $CH_2S$)-1H at 3.34 ppm (D, J=17 Hz, $CH_2S$)-6H at 1.41 ppm (2S,

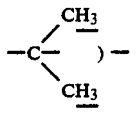

NMR n° 97

1H at 10.82 ppm (S, ArNHCO)-1H at 9.47 ppm (D, J=9 Hz, NHCO)-3H at 8.10 ppm (S.e., $CH_2N^+H_3$)-2H at 7.95 ppm (D, J=8 Hz, H aromatics ortho SCO)-2H at 7.72 ppm (D, J=8 Hz, H aromatics metal SCO)-2H at 7.20 ppm (S.e., $NH_2$ thiazole)-1H at 6.74 ppm (S, H thiazole)-1H at 5.76 ppm (D of D, $J_1$=9 Hz, $J_2$=4 Hz, $H_7$)-1H at 5.08 ppm (D, J=4 Hz, $H_6$)-2H at 4.55 ppm (S, $CH_2ON$)-1H at 4.27 ppm (D, J=13 Hz, $CH_2SCO$)-1H at 3.92 ppm (D, J=13 Hz, $CH_2SCO$)-2H at 3.81 ppm (S.e., $CH_2N^+H_3$)-1H at 3.71 ppm (D, J=17 Hz, $CH_2S$)-1H at 3.40 ppm (D, J=17 Hz, $CH_2S$)-.

The products according to the invention have been tested as regards their pharmacological properties and more particularly their bacteriostatic action. This action was determined in vitro by the dilutions method. The test was conducted both on positive Gram strains and no negative Gram strains.

The results, expressed in minimum inhibiting concentrations (CMI - μg/ml), are given in Table V.

TABLE V

| Products SR no | STRAINS Smith Staphylococcus | *Escherichia Coli* Col $E_1$ Amp | *Escherichia Coli* Sol RL 90 | Klebsiella R 30 | Enterbactor R 046 | *Proteus morganii* 1510 | Providencia 155 | *Pseudomonas aeruginosa* NCTC 8203 |
|---|---|---|---|---|---|---|---|---|
| 42317 | 0,25 | — | 1 | 8 | 1 | 8 | 1 | 16 |
| 42319 | 4 | — | 4 | 1 | 16 | 16 | 2 | 2 |
| 42800 | 8 | 0,0625 | 0,5 | 0,25 | 64 | 8 | 0,5 | 2 |
| 42801 | 4 | ≦0,0312 | 0,5 | 0,25 | 16 | 2 | 1 | 2 |
| 42802 | 4 | 0,0625 | 0,5 | 0,5 | — | 32 | 4 | 2 |
| 42803 | 4 | 0,0625 | 1 | 0,25 | 64 | 16 | 1 | 2 |
| 42804 | 8 | 0,0625 | 1 | 0,5 | 64 | 16 | 1 | 2 |
| 42808 | 2 | 0,25 | 1 | 0,5 | 64 | 16 | 1 | 1 |
| 42809 | 2 | 0,0625 | 1 | 0,5 | 64 | 16 | 1 | 1 |
| 42883 | 0,125 | 0,0625 | 1 | 2 | 16 | 2 | 1 | 8 |
| 42885 | 25 | ≦0,0312 | 0,25 | 2 | 32 | 2 | 0,5 | 2 |
| 42889 | 0,125 | ≦0,0312 | 1 | 2 | 16 | 8 | 2 | 32 |
| 42893 | 0,125 | 0,125 | 0,125 | 2 | 8 | 2 | 1 | 8 |
| 42895 | 0,5 | ≦0,0312 | 0,125 | 2 | 8 | 2 | 2 | 8 |
| 42897 | 0,5 | ≦0,0312 | 0,125 | 1 | 8 | 2 | 1 | 8 |
| 42880 | 8 | 0,0625 | 1 | 2 | 64 | 16 | 1 | 4 |
| 42882 | 2 | 0,0625 | 1 | 0,5 | 64 | 32 | 1 | 8 |
| 42943 | 2 | 0,0625 | 1 | 1 | 64 | 32 | 2 | 8 |
| 42946 | 1 | ≦0,0312 | 0,25 | 2 | 16 | 2 | 1 | 8 |
| 42965 | 1 | ≦0,0312 | 0,125 | 0,5 | 4 | 1 | 0,125 | 2 |
| 42967 | 0,125 | 0,0625 | 1 | 16 | 32 | 8 | 2 | 16 |
| 43015 | 4 | 0,0625 | 2 | 1 | — | 16 | 1 | 4 |
| 43016 | 2 | 0,0625 | 0,25 | 0,5 | 32 | 8 | 0,5 | 2 |
| 43019 | 4 | ≦0,0312 | 1 | 1 | 64 | 32 | 1 | 2 |
| 43027 | 0,125 | ≦0,0312 | 1 | — | 32 | 8 | 1 | 2 |
| 43029 | 0,5 | 0,0625 | 0,5 | 2 | 16 | 2 | 1 | 16 |
| 43147 | 1 | ≦0,0312 | 0,25 | 1 | 16 | 2 | 0,5 | 8 |
| 43179 | 0,5 | 0,0625 | 1 | 1 | 8 | 1 | 1 | 16 |
| 43183 | 1 | ≦0,0312 | 0,125 | 1 | 16 | 1 | 0,5 | 16 |
| 43185 | 1 | ≦0,0312 | 0,25 | 2 | 16 | 2 | 1 | 4 |
| 43187 | 0,125 | ≦0,0312 | 0,25 | 2 | 16 | 2 | 1 | 4 |
| 43189 | 0,125 | ≦0,0312 | 0,125 | 4 | 16 | 2 | 0,5 | 1 |
| 43191 | 0,125 | ≦0,0312 | 1 | 16 | 32 | 8 | 1 | 4 |
| 43226 | 0,25 | ≦0,0312 | 0,125 | 1 | 8 | 1 | 0,25 | 2 |
| 43323 | 1 | ≦0,0312 | 0,5 | 1 | 16 | 2 | 1 | 8 |
| 43336 | 1 | ≦0,0312 | 0,5 | 2 | 32 | 2 | 0,5 | 16 |
| 43417 | 0,5 | ≦0,0312 | 0,25 | 1 | 8 | 1 | 0,5 | 4 |
| 43419 | 0,5 | ≦0,0312 | 0,5 | 2 | 8 | 2 | 1 | 8 |

TABLE V-continued

| Products SR no | STRAINS Smith Staphy-lococcus | *Escherichia Coli* Col $E_1$ Amp | *Escherichia Coli* Sol RL 90 | Klebsiella R 30 | Enterbactor R 046 | *Proteus morganii* 1510 | Providencia 155 | *Pseudomonas aeruginosa* NCTC 8203 |
|---|---|---|---|---|---|---|---|---|
| 43464 | 1 | ≦0,0312 | 0,25 | 2 | 16 | 2 | 1 | 16 |
| 43520 | 0,125 | 0,0625 | 0,5 | 8 | 32 | 8 | 1 | 2 |
| 43559 | 0,5 | ≦0,0312 | 0,125 | 1 | 8 | 1 | 0,5 | 2 |
| 43666 | 0,5 | ≦0,0312 | 0,5 | 4 | 32 | 4 | 1 | 4 |

The results given in Table V show that the products according to the invention have a wide spectrum of activity, both on positive Gram bacteria and on negative Gram bacteria.

Moreover, according to the tests conducted on animals, the toxicity of these products appears to be sufficiently small to allow their use in therapeutics.

The products according to the invention can therefore be used as antibiotics in human and veterinary medicine. They have a wide spectrum and can be used in all bacterial infections with sensitive germs.

The products can be administrated by general route (perenteral or oral) or by local route.

The pharmaceutical compositions are produced from compounds (I) in a soluble form obtained by salification of one of the acid functions of the molecule or of one of the amine functions of chain B.

The pharmaceutical compositions containing, as active ingredient, the antibiotic according to the invention in combination with a pharmaceutically acceptable vehicle, may be solid or liquid; for example, they may be presented as injectable preparations, as tablets, gelules, granules, ointments, creams, gels or suppositories. Their posology may vary in a wide proportion, depending in particular on the type of gravity of the injection to be treated and depending on the mode of administration. In an adult, the posology is mostly between 0.250 g and 4 g per day by injectable route.

As an example of galenic preparation, it is possible to prepare an injectable solution, for every ampulla:

| | |
|---|---|
| SR 43189 | 1 g |
| Water for injectable preparation | 5 ml |
| Sodium carbonate s.q. for pH = | 6.3. |

We claim:

1. Celphalosporin compounds of the general formula:

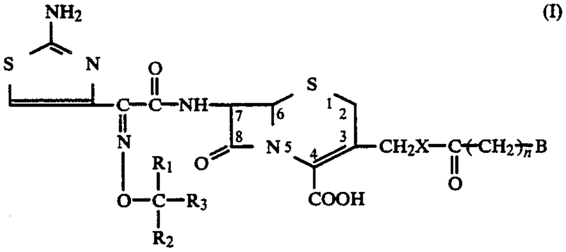

(I)

in which:

x is an oxygen atom or a sulfur atom $R_1$, $R_2$, and $R_3$ each designate, a hydrogen atom or else $R_1$ and $R_2$ designate a hydrogen atom or a methyl group, and $R_3$ designates a carboxyl or cyclopropyl group or else $R_1$ and $R_2$ taken together with the carbon atom to which they are linked form a cyclobutyl or cyclopentyl group and $R_3$ is a carboxyl group, B is the residue of a primary or secondary amine selected from the following groups:

$Z-NH_2$ where Z is an alkylene group with a straight or branched chain having from 2 to 7 carbon atoms, possibly interrupted by a sulfur atom, or else Z is a 1,3-cyclohexylene or 1,4 cyclohexylene group and n is zero, 1 or 2, Z'—Alk—NH—R where Z' is a 1,2-phenylene or 1,3-phenylene or 1,4-phenylene group possibly substituted by 1, 2 or 3 methyl groups or else Z' is a 1,2-cyclohexylene, pb 1,3-cyclohexylene or 1,4-cyclohexylene group, n is 1 or 2, Alk is a straight or branched alkyl group having from 2 to 3 carbon atoms, possibly interrupted by a sulfur atom, and R is a hydrogen atom or an alkyl group having from 1 to 3 carbon atoms,

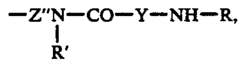

where Z" is a 1,3 phenylene or 1,4 phenylene group, Y is an alkyl group $(CH_2)_m$ in which m=1,2 or 3, R' is hydrogen or methyl, n is zero, 1 or 2 and R is as defined above, —Z"—CO—NH—Y—$NH_2$ where Z" and Y are as defined above and n is zero, 1 or 2, —Z"—Y'—NH—CO—Y—$NH_2$ where Z" and Y are as defined above and Y' is a straight or branched alkyl group with 1 or 2 carbon atoms,

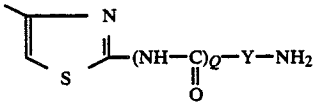

where O=0 or 1, n is zero, 1 or 2 and Y is as defined above, a 2-piperidyl, 3-piperidyl or 4-piperidyl group possibly substituted in the nitrogen atom by a —CO—Y—$NH_2$ group where Y is as defined above and n is zero, 1 or 2, a group

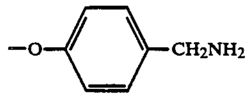

wherein n is zero, 1 or 2, the bicyclic group

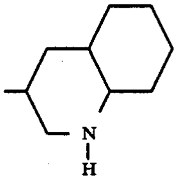

wherein n is zero, 1 or 2, as well as the pharmaceutically acceptable salts and esters thereof.

2. Antibiotic composition containing a cephalosporin derivative as claimed in claim 1, in combination with a pharmaceutically acceptable vehicle.

* * * * *

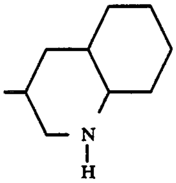

wherein n is zero, 1 or 2, as well as the pharmaceutically acceptable salts and esters thereof.

2. Antibiotic composition containing a cephalosporin derivative as claimed in claim 1, in combination with a pharmaceutically acceptable vehicle.

* * * * *